United States Patent
Bayer et al.

(10) Patent No.: US 9,861,758 B2
(45) Date of Patent: Jan. 9, 2018

(54) DRIVE MECHANISM OF A DRUG DELIVERY DEVICE

(71) Applicant: Sanofi, Paris (FR)

(72) Inventors: Stefan Bayer, Würselen (DE); Daniel Berning, Baesweiler (DE); Philippe Blank, Düsseldorf (DE); Wolfgang Pelzer, Kreuzau (DE); Michael Pfoser, Kohlscheid (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 150 days.

(21) Appl. No.: 14/782,706

(22) PCT Filed: Apr. 8, 2014

(86) PCT No.: PCT/EP2014/056972
§ 371 (c)(1),
(2) Date: Oct. 6, 2015

(87) PCT Pub. No.: WO2014/166894
PCT Pub. Date: Oct. 16, 2014

(65) Prior Publication Data
US 2016/0067412 A1 Mar. 10, 2016

(30) Foreign Application Priority Data
Apr. 10, 2013 (EP) .................................. 13163072

(51) Int. Cl.
*A61M 5/00* (2006.01)
*A61M 5/315* (2006.01)

(52) U.S. Cl.
CPC ...... *A61M 5/3158* (2013.01); *A61M 5/31541* (2013.01); *A61M 5/31548* (2013.01);
(Continued)

(58) Field of Classification Search
CPC .......... A61M 5/31541; A61M 5/31551; A61M 5/31553; A61M 5/31533; A61M 5/3155;
(Continued)

(56) References Cited

U.S. PATENT DOCUMENTS

| 2003/0160072 A1* | 8/2003 | Geiser ..................... A61M 5/24 222/327 |
| 2006/0167419 A1* | 7/2006 | Fiechter ............ A61M 5/31553 604/181 |

(Continued)

FOREIGN PATENT DOCUMENTS

EP 2 275 158 1/2011

OTHER PUBLICATIONS

International Preliminary Report on Patentability in International Application No. PCT/EP2014/056972, dated Oct. 13, 2015, 8 pages.

(Continued)

*Primary Examiner* — Emily Schmidt
(74) *Attorney, Agent, or Firm* — Fish & Richardson P.C.

(57) ABSTRACT

A drug delivery device for dispensing a dose of a medicament includes an elongated housing extending in an axial direction, and a piston rod to operably engage with a piston of a cartridge to displace the piston in a distal axial direction. The drug delivery device further includes a drive sleeve extending in an axial direction and being rotatable against the action of a spring during a dose setting procedure and a dispensing sleeve rotatably engaged with the piston rod and being displaceable in an axial direction relative to the drive sleeve to engage with the drive sleeve in a torque transmissive way during a dose dispensing procedure.

29 Claims, 13 Drawing Sheets

(52) U.S. Cl.
CPC .... *A61M 5/31585* (2013.01); *A61M 5/31593* (2013.01); *A61M 5/31553* (2013.01); *A61M 5/31563* (2013.01); *A61M 5/31568* (2013.01); *A61M 2205/581* (2013.01)

(58) Field of Classification Search
CPC .......... A61M 5/31528; A61M 5/31555; A61M 5/31548; A61M 5/3158; A61M 5/31585
See application file for complete search history.

(56) References Cited

U.S. PATENT DOCUMENTS

| | | | |
|---|---|---|---|
| 2011/0004166 A1* | 1/2011 | Wittmann | A61M 5/20 604/207 |
| 2011/0054412 A1 | 3/2011 | Eich et al. | |

OTHER PUBLICATIONS

International Search Report and Written Opinion in International Application No. PCT/EP2014/056972, dated Aug. 5, 2014, 10 pages.
Rote Liste, "50. Hypophysen-, Hypothalamushormone, andere regulatorische Peptide u. ihre Hemmstoffe," Chapter 50, ed. 2008, 20 pages.

* cited by examiner

A-A

B-B

C-C

D-D

E-E

F-F

G-G

H-H

DRIVE MECHANISM OF A DRUG DELIVERY DEVICE

CROSS-REFERENCE TO RELATED APPLICATIONS

This application is a national stage application under 35 U.S.C. §371 of International Patent Application No. PCT/EP2014/056972, filed on Apr. 8, 2014, which claims priority to EP 13163072.5, filed on Apr. 10, 2013. The entire contents of each of the foregoing applications are incorporated herein by reference.

The present invention relates to a drive mechanism for a drug delivery device and to a respective drug delivery device. In particular, the invention relates to an injection device such like a pen-type injector inter alia comprising a single and/or a last-dose limiting mechanism and further comprising a comparatively large dose indicating display.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a set dose is entirely injected. There already exist some drug delivery devices with end-of-content mechanisms or last dose mechanisms.

Drug delivery devices such like pen type injectors also provide a dose indicating mechanism which is operable to display the size of a set dose to a user. Typically, the housing of such drug delivery devices comprises a dose indicating window where a number representing the size of the dose shows up.

Especially with elderly or visually impaired patients, reading of such dose indicating numbers if sometimes difficult. With devices adapted for injection of e.g. insulin, typical dose sizes may vary between 0 and 120 I.U. (International Units) of insulin. Due to the rather compact design and limited geometrical dimensions of such drug delivery devices the size of such dose indicating numbers is fairly small. For visually impaired persons reading of such tiny numbers may therefore be rather difficult. However, since such drug delivery devices are intended for self-medication treatment, it is of importance, that the user is able to correctly determine the size of dose actually set.

OBJECTS OF THE INVENTION

It is therefore an object of the present invention to avoid disadvantages of known drug delivery devices and to provide a drive mechanism of a drug delivery device allowing for an intuitive operation, both for setting and for dispensing of a dose. It is another object to provide a dose indicating mechanism which is easy and unequivocal to read even for persons suffering impaired vision.

In another object, the invention serves to provide a drive mechanism of a drug delivery device for setting and dispensing of a dose of a medicament and further featuring a single dose limited mechanism and a last dose limiting mechanism.

It is a further aim to provide a drug delivery device comprising such a drive mechanism and comprising a cartridge sealed with a piston and being operably engaged with a piston rod of such drive mechanism.

SUMMARY OF THE INVENTION

In a first aspect a drive mechanism of a drug delivery device is provided for dispensing of a dose of a medicament. The drive mechanism comprises an elongated housing extending in an axial direction. Typically, the housing is of substantially tubular or cylindrical shape that allows gripping and operating of the drive mechanism and of the drug delivery device by only one hand of a user.

The drive mechanism further comprises a piston rod to operably engage with a piston of a cartridge containing the medicament to be dispensed by the drive mechanism. The cartridge comprises a piston, typically at its proximal end, which, by means of a displacement in axial distal direction serves to expel an amount of the medicament from the cartridge. The piston typically seals the cartridge in axial proximal direction.

The piston rod of the drive mechanism serves to displace the piston of the cartridge in axial distal direction for expelling a predefined amount of the medicament from the cartridge. Hence, the piston rod is operable to apply distally-directed thrust or pressure to the piston of the cartridge for displacing the same in distal direction for a predetermined distance that corresponds to a respective amount or dose of the medicament to be dispensed.

The drive mechanism comprises a drive sleeve extending in axial direction and being rotatably supported in the housing. The drive sleeve is rotatable with regard to an axis of rotation substantially coinciding with the axial direction of the elongated housing. For setting of a dose, hence during a dose setting procedure, the drive sleeve is rotatable against the action of a spring. By rotating the drive sleeve in a dose setting direction, said spring, being engaged with the drive sleeve, is biased in order to store mechanical energy.

During a subsequent dose dispensing procedure, when the drive sleeve is released, it may then rotate in an opposite direction under the action of said spring for driving the piston rod in distal direction. Typically, the drive sleeve is operably disengaged or releasable from the piston rod for setting of a dose. During a dose setting procedure, the piston rod remains substantially stationary with respect to the housing while the drive sleeve, operably disconnected and released from the piston rod is rotatable relative to the housing and hence relative to the piston rod.

The drive mechanism further comprises a dispensing sleeve rotatably engaged with the piston rod and being displaceable in axial direction relative to the drive sleeve to engage with the drive sleeve in a torque transmissive way during a dose dispensing procedure. Here, the dispensing sleeve provides a double function. By way of an axial displacement relative to the drive sleeve, the dispensing sleeve can be selectively rotatably coupled with the drive sleeve, thereby switching the drive mechanism between a dose setting mode, in which dispensing sleeve and drive sleeve are disconnected and a dose dispensing mode, in which dispensing sleeve and drive sleeve are rotatably engaged.

Moreover, the dispensing sleeve serves as a torque transmission component to transfer a rotative motion of the drive sleeve to the piston rod during a dose dispensing procedure for driving the piston rod in distal direction.

The mutual engagement of drive sleeve, piston rod and dispensing sleeve allows for a rather compact and robust design of the drive mechanism. Due to the switching function and the torque transmission function of the dispensing sleeve, the overall number of parts the drive mechanism is assembled of can be reduced. This way, mechanical tolerances of the mutually interacting components of the drive mechanism can be reduced.

In a further embodiment, the drive sleeve is axially displaceable between a dose setting position and a dose dispensing position against the action of at least one drive sleeve spring element. Typically, the drive sleeve is displaceable in distal direction relative to the housing against the action of the at least one drive sleeve spring element. Typically, the dose dispensing position correlates and corresponds to a distal stop position of the drive sleeve whereas a dose setting position corresponds to a proximal stop position of the drive sleeve.

The drive sleeve is rotatable in a dose setting direction against the action of a helical spring when located in the dose setting position. By displacing the drive sleeve into the dose dispensing position, the drive sleeve may be allowed to rotate in the opposite, hence in a dose dispensing direction under the action of said helical spring. Typically, axially distally-directed displacement of the drive sleeve requires constant exertion of a respective distally-directed thrust or force acting on the drive sleeve to keep the same in the distal dose dispensing position. A decrease of said thrust or distally-directed dispensing force below a predetermined threshold typically leads to a returning of the drive sleeve into the dose setting position under the action of the at least one drive sleeve spring element. Hence, a premature release of e.g. an injection button, by way of which the drive sleeve is displaceable in axial distal direction, may immediately return the drive sleeve into its dose setting position. This way, premature release of an injection button and hence of a drive sleeve axially coupled therewith may instantly interrupt a dose dispensing procedure.

In a further embodiment, the dispensing sleeve is displaceable in axial distal direction to axially engage with the drive sleeve in an intermediate position. Typically, the drive sleeve and the dispensing sleeve comprise mutually engaging and radially extending portions, such like stop faces by way of which a distally-directed displacement of the dispensing sleeve may correspondingly transfer to a respective distally-directed displacement of the drive sleeve.

In the intermediate position, dispensing sleeve and drive sleeve may mutually abut or mutually engage in axial direction. A further displacement of the dispensing sleeve into a distal stop position of the dispensing sleeve may then transfer and/or slave the drive sleeve from the dose setting position into the dose dispensing position. Here, the dispensing sleeve serves as a dispensing clutch by way of which the drive sleeve can be pushed from its dose setting position into the dose dispensing position against the action of the drive sleeve spring element.

Typically, mutual engagement and axial displacement of dispensing sleeve and drive sleeve is characterised by two subsequent steps of displacement. In a first step, the dispensing sleeve is displaceable in axial direction until it reaches the intermediate position, in which it axially and/or rotatably engages with the drive sleeve. During this first step and during such an initial movement of the dispensing sleeve, the drive sleeve remains substantially stationary. Due to the mutual axial and/or rotational engagement of drive sleeve and dispensing sleeve the drive sleeve can be slaved to the dispensing sleeve during the subsequent second displacement step, during in which the dispensing sleeve is further displaceable into a distal stop position.

During this second step of axial displacement, the dispensing sleeve is operable to push the drive sleeve in distal direction to reach its dose dispensing position. During this distally-directed displacement of the drive sleeve the drive sleeve is operably engaged, typically rotatably locked to the dispensing sleeve.

In typical embodiments, the drive sleeve is rotatable in the dose setting direction relative to the housing in a step-wise incrementing way against the action of a helical spring. This rotative displacement is typically controlled by a ratchet mechanism, which serves to keep the drive sleeve in a rotated position and to hinder that the drive sleeve immediately returns into an initial configuration, which may resemble a zero dose configuration. It is due to the axial displacement of the drive sleeve from its dose setting position into its dose dispensing position that the drive sleeve is released and disengaged from the ratchet mechanism.

Hence, when displaced in axial distal direction to the dose dispensing position the drive sleeve is free to rotate under the action of the previously biased helical spring.

Since the drive sleeve is already rotatably engaged with the dispensing sleeve before it reaches the distal dose dispensing position, the rotation of the drive sleeve relative to the housing equally transfers to a respective rotation of the dispensing sleeve. Since the dispensing sleeve is permanently rotatably engaged with the piston rod, also the piston rod will rotate during a dose setting procedure and may therefore be advance in distal direction for driving the piston of the cartridge accordingly.

In a further embodiment, the dispensing sleeve is axially displaceable relative to the drive sleeve against the action of at least one dispensing sleeve spring element. Under the action of said dispensing sleeve spring element, the dispensing sleeve can return into an initial axial position, in which dispensing sleeve and drive sleeve are operably disconnected. Typically, the drive sleeve is displaceable from the dose setting position to the dose dispensing position against the action of a drive sleeve spring element, which may extend between the drive sleeve and the housing.

A further spring element, e.g. a dispensing sleeve spring element may be additionally provided between the drive sleeve and the dispensing sleeve. The spring constants of said drive sleeve spring element and the dispensing sleeve spring element substantially differ so that an almost full compression of the dispensing sleeve spring element may already be attained before the drive sleeve spring element is biased. By appropriately selecting the spring constants of the drive sleeve spring element and the dispensing sleeve spring element a mutual and torque transmitting engagement of drive sleeve and dispensing sleeve can be attained even before the drive sleeve reaches its distal dose dispensing position.

According to another embodiment the inside wall of the dispensing sleeve and a proximal end section of the piston rod are mutually engaged by means of at least one axially and radially extending protrusion engaging with a correspondingly shaped axially and radially extending recess. Hence, the dispensing sleeve and the piston rod are directly mechanically engaged in a splined way by means of at least one axially extending groove or notch receiving a correspondingly shaped protrusion. Piston rod and dispensing sleeve are rotatably locked and are axially displaceable relative to each other.

For instance, the dispensing sleeve comprises at least one, preferably at least two diametrically oppositely located radially outwardly extending and axially elongated notches or grooves at an inside wall portion in which correspondingly shaped and radially outwardly extending protrusions or pins of the piston rod are received. In this way, a permanent rotational engagement between dispensing sleeve and piston rod can be attained while the dispensing sleeve is displaceable in axial direction relative to the piston rod.

Therefore, axial displacement of the dispensing sleeve, either in distal or proximal direction has no substantial influence on the position of the piston rod. It is only due to a threaded engagement of the piston rod with the housing, that a rotative movement of the dispensing sleeve relative to the housing is transferred to the piston rod for driving the same in distal direction during a dose dispensing procedure.

It is generally also conceivable, that it is the inside wall of the dispensing sleeve which comprises at least one radially inwardly extending protrusion to engage with at least one correspondingly and radially inwardly extending recess or groove of the piston rod.

In order to homogeneously distribute a torque transmission between the piston rod and the hollow dispensing sleeve is it of particular benefit, that the rotatable engagement of dispensing sleeve and piston rod comprises at least two or more diametrically oppositely located or homogeneously distributed mutually engaging protruding and recessed structures.

In a further embodiment, the dispensing sleeve extends radially between the piston rod and the drive sleeve. The hollow dispensing sleeve receives the piston rod therein. The dispensing sleeve therefore provides a kind of bearing and guiding function for the piston rod. Additionally, at least a distal end of the dispensing sleeve extends into the drive sleeve in order to selectively engage with the drive sleeve and in order to axially abut with the drive sleeve for driving the same into the distal dose dispensing position in the event of a dose dispensing action.

Hence, drive sleeve and dispensing sleeve are at least partially interleaved. In this way, dispensing sleeve and drive sleeve may mutually mechanically stabilize. Moreover, the dispensing sleeve and the drive sleeve may comprise axially extending guiding structures by way of which a well defined axial mutual displacement of drive sleeve and dispensing sleeve can be realized. In this way, a mutual and selective torque transmitting coupling of drive sleeve and dispensing sleeve can be attained.

In another embodiment, the dispensing sleeve is displaceable in distal direction from a proximal dose setting position into a distal dose dispensing position by means of an axially depressable injection button located at a proximal end of the housing of the drive mechanism. The injection button typically closes a proximal end of the drive mechanism's housing. Typically, the proximal end of the dispensing sleeve extends into the injection button, so that a distally-directed depression of said button directly induces a correspondingly directed distal displacement of the dispensing sleeve.

A proximal end of the dispensing sleeve may further engage with the drive sleeve in a torque transmissive way when the drive sleeve reaches the above mentioned intermediate position. By means of a further and combined displacement of dispensing sleeve and drive sleeve, a rotational interlock of the drive sleeve may be released so that mechanical energy stored in the helical spring during a dose setting procedure can be released to set the drive sleeve in a dose dispensing directed rotation.

The rotation of the drive sleeve may be equally transferred to the dispensing sleeve and to the piston rod rotatably engaged therewith. The piston rod is threadedly engaged with the housing. Therefore, a rotation of the piston rod inherently comes along with a distally-directed displacement of the piston rod relative to the housing.

Typically, the dispensing sleeve is depressable in distal direction against the action of the dispensing sleeve spring element: Moreover, an injection spring may be arranged between the dispensing sleeve and the injection button or may be alternatively arranged between the injection button and the housing. By means of the injection spring, the injection button may return into a proximally-directed initial position as soon as a user no longer depresses said button.

According to another embodiment a distal end of the dispensing sleeve is releasably rotatably locked with a distal end of the drive sleeve when the dispensing sleeve is in the intermediate position. A clutch to releasably and rotatably engage dispensing sleeve and drive sleeve is located at the distal ends of dispensing sleeve and drive sleeve, respectively. In this way, the dispensing sleeve is axially displaceable between the dose setting position, in which it is released from the drive sleeve, into the intermediate position and further into the dose dispensing position.

When arriving in the intermediate position the dispensing sleeve rotatably engages or rotatably locks with the drive sleeve. While being rotatably locked a further distally-directed displacement of the dispensing sleeve leads to a corresponding distally-directed displacement of the drive sleeve until the drive sleeve reaches the dose dispensing position. In the dose dispensing position, the drive sleeve is free to rotate relative to the housing under the action of the helical spring that is typically biased during a dose setting procedure.

The dispensing sleeve has a twofold functionality. Since it is permanently rotatably engaged with the piston rod it serves as a kind of a drive member to set the piston rod in rotation during and for a dose dispensing procedure. Further and due to the axial displacement relative to the piston rod and relative to the housing the dispensing sleeve also provides axial thrust transfer across the drive mechanism in order to selectively release and engage a rotational coupling between the drive sleeve and the piston rod.

According to another embodiment the drive sleeve is axially displaceable relative to the housing in distal direction from the dose setting position into the dose dispensing position against the action of a drive sleeve spring element. In the dose setting position the drive sleeve is rotatably locked to the housing, typically by way of a clutch or ratchet mechanism. By displacing the drive sleeve in distal axial direction relative to the housing said clutch or ratchet mechanism is released so that the drive sleeve is free to rotate under the action of the helical spring when reaching the dose dispensing position, which typically corresponds to a distal stop position.

This distally-directed displacement, which may be induced by the axial sliding displacement of the dispensing sleeve is conducted against the action of the drive sleeve spring element, which is typically located between a distal end of the drive sleeve and a radially inwardly extending protrusion or rim of the housing. The drive sleeve spring element serves to return the drive sleeve into its dose setting position as soon as an axially and distally-directed dispensing force is no longer present.

According to a further embodiment the dispensing sleeve is axially displaceable relative to the housing. Moreover, the dispensing sleeve is also permanently rotatably engaged with the piston rod. The permanent rotational engagement between the dispensing sleeve and the piston rod allows that the dispensing sleeve is axially displaceable, hence axially slidable relative to the piston rod as well as relative to the housing. When initially depressed in distal direction, e.g. by means of a proximally located injection button, the dispensing sleeve is distally displaceable relative to the housing and relative to the drive sleeve against the action of the dispensing sleeve spring element, which is typically located between the dispensing sleeve and the drive sleeve.

By means of the dispensing sleeve spring element a torque transferring clutch between the dispensing sleeve and the drive sleeve can either be closed or activated, typically, when the dispensing sleeve spring element is compressed. Upon release and upon axial extension of the dispensing sleeve spring element the dispensing sleeve is displaceable relative to the drive sleeve in proximal direction so as to release a torque transmissive or rotative coupling thereof.

When the dispensing sleeve is in the intermediate position the dispensing sleeve spring element is typically compressed so that the clutch or coupling between the dispensing sleeve and the drive sleeve is closed or active. A further distally-directed displacement of the dispensing sleeve relative to the housing then serves to push and to slave the drive sleeve also in distal direction so as to liberate and to release a clutch or ratchet mechanism acting between the drive sleeve and the housing.

As soon as the drive sleeve is released to rotate relative to the housing this rotation is equally transferred to the dispensing sleeve and hence to the piston rod, which due to its threaded engagement with a threaded support of the housing is driven in distal direction for dispensing of a dose.

In still another embodiment a proximal end of the piston rod is rotatably locked with the dispensing sleeve while a distal end of the piston rod comprises an outer thread by way of which it is threadedly engaged with a threaded support of the housing. A rotational lock between piston rod and dispensing sleeve is also attainable by means of at least one longitudinally or axially extending slit intersecting the outer thread of the piston rod, wherein a radially inwardly extending protrusion of the dispensing sleeve engages with this slit.

In this way, the dispensing sleeve and the piston rod are rotatably locked in order to unequivocally transfer a torque or a rotative movement of the dispensing sleeve towards the piston rod. Such a rotational locking or rotational coupling may be permanent. Due to its threaded engagement with the housing's threaded support the piston rod advances in a screw-like motion in distal direction when the dispensing sleeve is subject to rotation. Since the piston rod and the dispensing sleeve are axially slidably engaged, the piston rod may can advance in distal direction while the dispensing sleeve rests in the distal stop position or in the dose dispensing position.

In a further embodiment the drive mechanism also comprises a dose dial button rotatably supported at the proximal end of the housing and being selectively rotatably engageable with a dose setting sleeve extending in axial direction. The dose dial button may comprise a geometric shape of a sleeve effectively surrounding a distal end of the cup-shaped dispensing button. The dose dial button is axially fixed to the housing and may be rotated either clockwise or counter clockwise for setting of a dose. Setting of a dose refers to both, incrementing of a dose as well as decrementing of a dose in the event, that a selected dose should be too large and has to be corrected in size.

The dose dial button is rotatably engaged with the dose setting sleeve when the drive mechanism is in a dose setting mode. In a dose dispensing mode of the drive mechanism, the dose dial button may be disengaged from the dose setting sleeve. In this way, a counter-directed dose dispensing rotation of e.g. the drive sleeve has no influence on the dose dial button.

Typically and according to another embodiment, a distal end of the dose setting sleeve is rotatably engaged with the drive sleeve, when the drive sleeve is in dose setting position. The dose setting sleeve therefore serves to transfer the angular momentum of the dose dial button to the drive sleeve during a dose setting procedure. Since the dose dial button is operably disconnected from the dose setting sleeve when the drive mechanism is in injection mode, the dose setting sleeve does not necessarily have to be disconnected from the drive sleeve. Generally, the dose setting sleeve could be permanently connected and engaged with the drive sleeve.

The dose setting sleeve is only selectively engaged with the drive sleeve when the drive mechanism is in dose setting mode. In dose dispensing mode the dose setting sleeve is typically disengaged and released from the drive sleeve, when the drive sleeve is released and is allowed to rotate in a dose dispensing direction. The selective coupling of dose setting sleeve and drive sleeve is beneficial in terms of providing a last dose limiting mechanism as will be explained below.

A torque transmissive and rotational engagement of the dose setting sleeve and the drive sleeve is obtainable by a direct and mutual engagement of the dose setting sleeve's distal end section with a proximal end section of the drive sleeve. In order to allow for a rather compact design of the drive mechanism the dose setting sleeve and the drive sleeve co-align in axial direction. A mutual torque transmissive engagement of dose setting sleeve and drive sleeve may then be provided by mutually corresponding crown wheel portions at the distal end face of the dose setting sleeve and the proximal end face of the drive sleeve.

The dose setting sleeve is axially fixed relative to the housing. This means, the dose setting sleeve remains stationary relative to the housing in both, the dose setting mode and the dose dispensing mode. It is typically the drive sleeve which is selectively displaceable in distal direction to transfer the drive mechanism into the dose dispensing mode, thereby disengaging the mutually corresponding crown wheel portions of the dose setting sleeve and the drive sleeve.

By disengaging the drive sleeve and the dose setting sleeve in the dose dispensing mode of the drive mechanism, the dose setting sleeve will not rotate in a dose dispensing direction during a dose dispensing procedure. This allows to implement a last dose limiting mechanism on the basis of the dose setting sleeve which is only operable and which will exclusively rotate during a dose setting operation of the drive mechanism.

In a further embodiment the drive mechanism also comprises a dose indicating mechanism for displaying a size of the dose actually set by the drive mechanism. The dose indicating mechanism comprises a base rotatably supporting a first spool and a second spool at a predefined distance with respect to each other and in a substantially parallel orientation.

First and second spools extend in axial direction. Hence, first and second spools rotate about respective axis of rotations which extend parallel to the longitudinal direction or the axial direction of the housing. First and second spools are arranged at a radial distance from the piston rod and/or from the drive sleeve. The spools are typically arranged radially outside the drive sleeve. They are positioned beneath the housing and may be arranged in substantially identical or at least partially overlapping axial positions with respect to each other.

The dose indicating mechanism further comprises a dose indicating tape or belt which is coiled onto at least the second spool in an initial, hence zero dose configuration. Said dose indicating tape is further fixed with another end to an outer circumference of the first spool. The dose indicating tape therefore extends between the first and second spools and can be selectively and alternately coiled onto first and second spools in an alternating way.

During a dose setting procedure the first spool is typically rotatably coupled with the drive sleeve, thereby coiling up the dose indicating tape to the first spool to a certain extent. Depending on the number of revolutions of the first spool during a dose setting procedure, the dose indicating tape will be transferred from the second spool towards the first spool.

The dose indicating mechanism is typically arranged inside the housing of the drive mechanism in such a way, that the dose indicating tape extending between first and second spools shows up below a dose indicating window of the housing. Since the dose indicating tape is selectively coiled up onto first and second spools, the tape can be rather long and may provide almost unlimited space for printing numbers thereon. The numbers presented on the dose indicating tape may therefore be comparatively large allowing for a good visibility and for a sufficient and unequivocal reading, even by patients or users suffering impaired vision.

In another embodiment, the second spool is rotatable relative to the base against the action of a spring while the first spool is permanently rotatably engaged with the drive sleeve. Hence, unwinding of the dose indicating tape from the second spool may only occur against the action of a respective spool spring. By means of the spool spring, the dose indicating tape can be sufficiently strained between first and second spools in order to stay free of any slacks.

Additionally, the spring spool serves to return the dose indicating tape onto the second spool in the event of a dose dispensing procedure. The numbers of the dose indicating tape that will show up in a dose indicating window of the housing will then decrement accordingly.

The rotative engagement of the first spool and the drive sleeve is invariant to a distally-directed displacement of the drive sleeve relative to the housing and/or relative to the at least first spool of the dose indicating mechanism. The first spool and the drive sleeve are rotatably engaged by means of gear wheels featuring an axial extension which allows for an axial displacement of the drive sleeve relative to the first spool when switching the drive mechanism between dose setting mode and dose dispensing mode. By means of the mutually engaging gearwheels of the first spool and the drive sleeve also a predefined transmission ratio regarding the revolutions of drive sleeve and first spool can be implemented.

In a further embodiment, the dose setting sleeve comprises an outer threaded section to threadedly engage with an inside facing thread of a last dose limiting member rotatably locked to the housing. The dose limiting member is splined with an inside facing side wall portion of the housing. Correspondingly, the last dose limiting member, which may be of semi-circular or arc shape is arranged radially between the dose setting sleeve and the housing. The last dose limiting member is splined to the housing, e.g. by means of at least one axially and radially extending protrusion engaging with a correspondingly shaped axially and radially extending recess.

It may be the last dose limiting member that comprises a radially outwardly extending protrusion to engage with a correspondingly shaped radially outwardly extending recess provided at an inside facing sidewall portion of the housing. However, also an opposite arrangement is conceivable, wherein an outer portion of the last dose limiting member comprises a recess to mate with a radially inwardly extending protrusion provided at an inside wall of the housing.

Since the dose setting sleeve is exclusively operable during dose setting, the dose limiting member experiences a distally-directed displacement along the housing when the dose setting sleeve is subject to rotation. This way, the axial position of the last dose limiting member relative to the dose setting sleeve may be indicative of the total amount of doses set and dispensed by the drive mechanism.

In a further embodiment also the drive sleeve comprises an outer threaded section to threadedly engage with an inside facing thread of a single dose limiting member which is rotatably locked to the housing. Similar as already described with respect to the last dose limiting member also the single dose limiting member may be rotatably locked to the housing by way of at least one axially and radially extending protrusion engaging with a correspondingly shaped axially and radially extending recess.

The protrusion may be provided at an outer circumference of the ring-shaped or semi-ring-shaped dose limiting member while the radially extending recess may be provided at an inside facing sidewall portion of the housing.

Since the drive sleeve is operable to rotate in a dose setting direction during dose setting and into an opposite dose dispensing direction during dose dispensing, the single dose limiting member will accordingly be displaced in distal and proximal direction during dose setting and dose dispensing, respectively.

In another embodiment, the last and/or the single dose limiting member abut with a radially outwardly extending radial stop of the dose setting sleeve and/or the drive sleeve, respectively. Typically, the last dose limiting member as well as the single dose limiting member comprise a trailing and a leading edge which may abut with correspondingly shaped radially outwardly extending stops of the last dose limiting member and/or the single dose limiting member when an end of content configuration or when a maximum dose setting configuration of the drive mechanism will be reached.

As soon as for instance the last dose limiting member gets in abutment with a last dose stop of the dose setting sleeve, a further dose incrementing rotation of the dose setting sleeve is blocked. Hence, a dose exceeding the amount of medicament left in the cartridge cannot be set. A dose setting procedure will then be stopped or interrupted accordingly.

The same may apply with the single dose limiting member during a dose setting procedure. When the single dose limiting member abuts with the radially outwardly extending radial stop of the drive sleeve, the drive sleeve cannot be further rotated in a dose setting direction. Consequently, a dose setting procedure will be limited and stop. In this way, setting of a dose exceeding a predefined dose size of e.g. 120 I.U. can be effectively prevented.

Since the drive sleeve is subject to a counter-directed dose dispensing rotation during a subsequent dose dispensing procedure, also the single dose limiting member will return into an initial axial position relative to the drive sleeve. Here, it is of particular benefit, when the single dose limiting member audibly engages with a zero dose stop when reaching an initial configuration that coincides with the termination or end of a dose dispensing procedure. By providing the single dose limiting member with a clicking element, reaching of a zero dose configuration may come along with an audible click sound indicating to a user, that the end of a dose dispensing procedure has been reached.

According to another aspect, the invention also relates to a drug delivery device for dispensing of a dose of a medicament. The drug delivery device comprises a drive mechanism as described above and a cartridge at least partially filled with the medicament to be dispensed by the drug delivery device. The cartridge is arranged in the housing of the drive mechanism or in a cartridge holder of the drug delivery device which is fixed to the housing either releasably or non-releasably, e.g. in case of a disposable drug delivery device. Consequently, the drug delivery device comprises a cartridge holder to receive and to accommodate a cartridge filled with the medicament.

Apart from that, the drug delivery device and the drive mechanism may comprise further functional components, such like an injection button, by way of which a user may trigger and control the drug delivery device and its drive mechanism for dispensing of a dose of the medicament.

In the present context, the distal direction points in the direction of the dispensing and of the device, where, a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
  H-(Lys)4-des Pro36, des Pro37 Exendin-4(1-39)-NH2,
  H-(Lys)5-des Pro36, des Pro37 Exendin-4(1-39)-NH2,
  des Pro36 Exendin-4(1-39),
  des Pro36 [Asp28] Exendin-4(1-39),
  des Pro36 [IsoAsp28] Exendin-4(1-39),
  des Pro36 [Met(O)14, Asp28] Exendin-4(1-39),
  des Pro36 [Met(O)14, IsoAsp28] Exendin-4(1-39),
  des Pro36 [Trp(O2)25, Asp28] Exendin-4(1-39),
  des Pro36 [Trp(O2)25, IsoAsp28] Exendin-4(1-39),
  des Pro36 [Met(O)14 Trp(O2)25, Asp28] Exendin-4(1-39), des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, various embodiments of the invention will be described by making reference to the drawings, in which.

DETAILED DESCRIPTION

Figure 1:
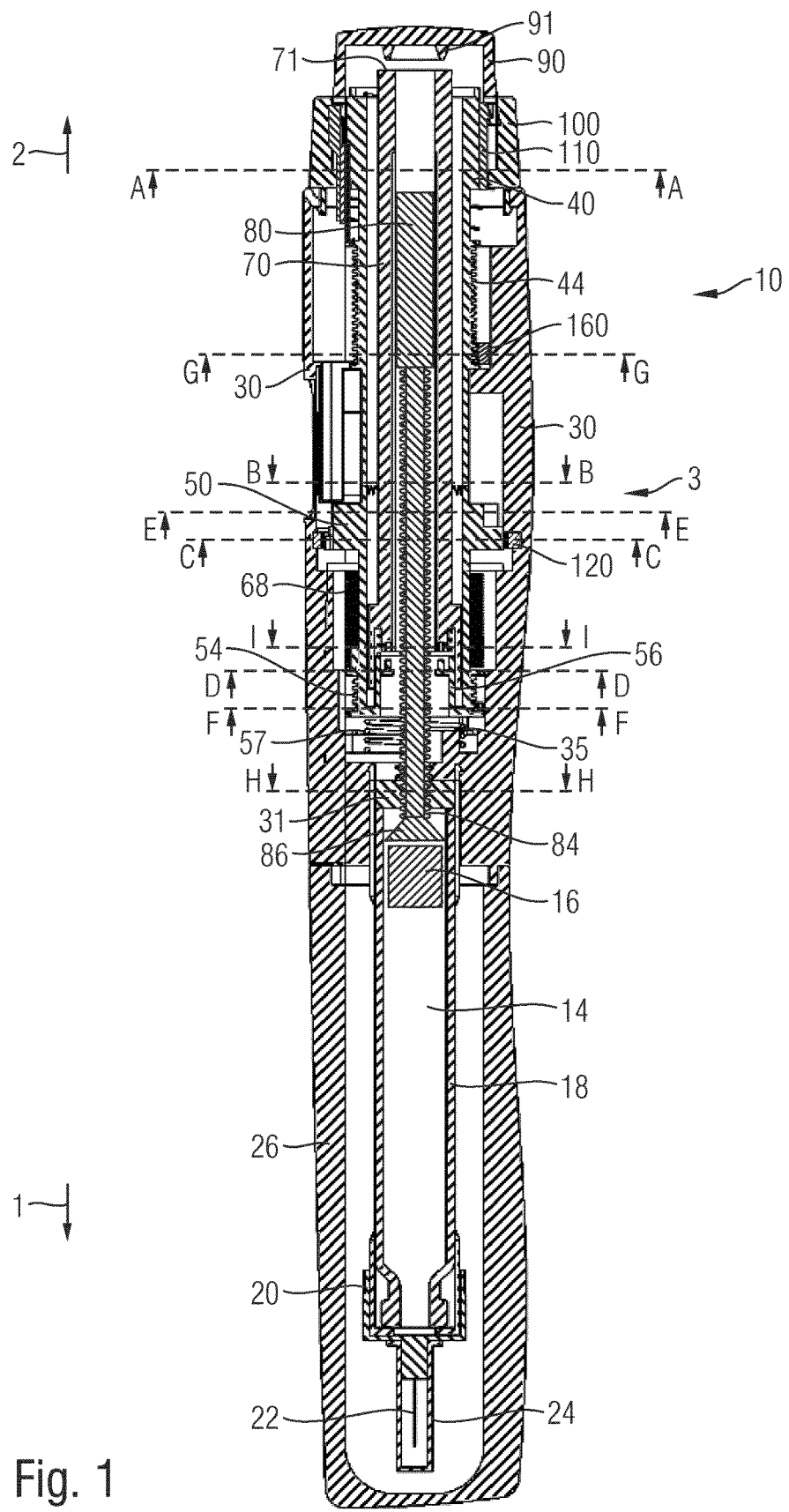
FIG. 1 schematically illustrates the assembled drug delivery device in a longitudinal cross section.
Figure 10:
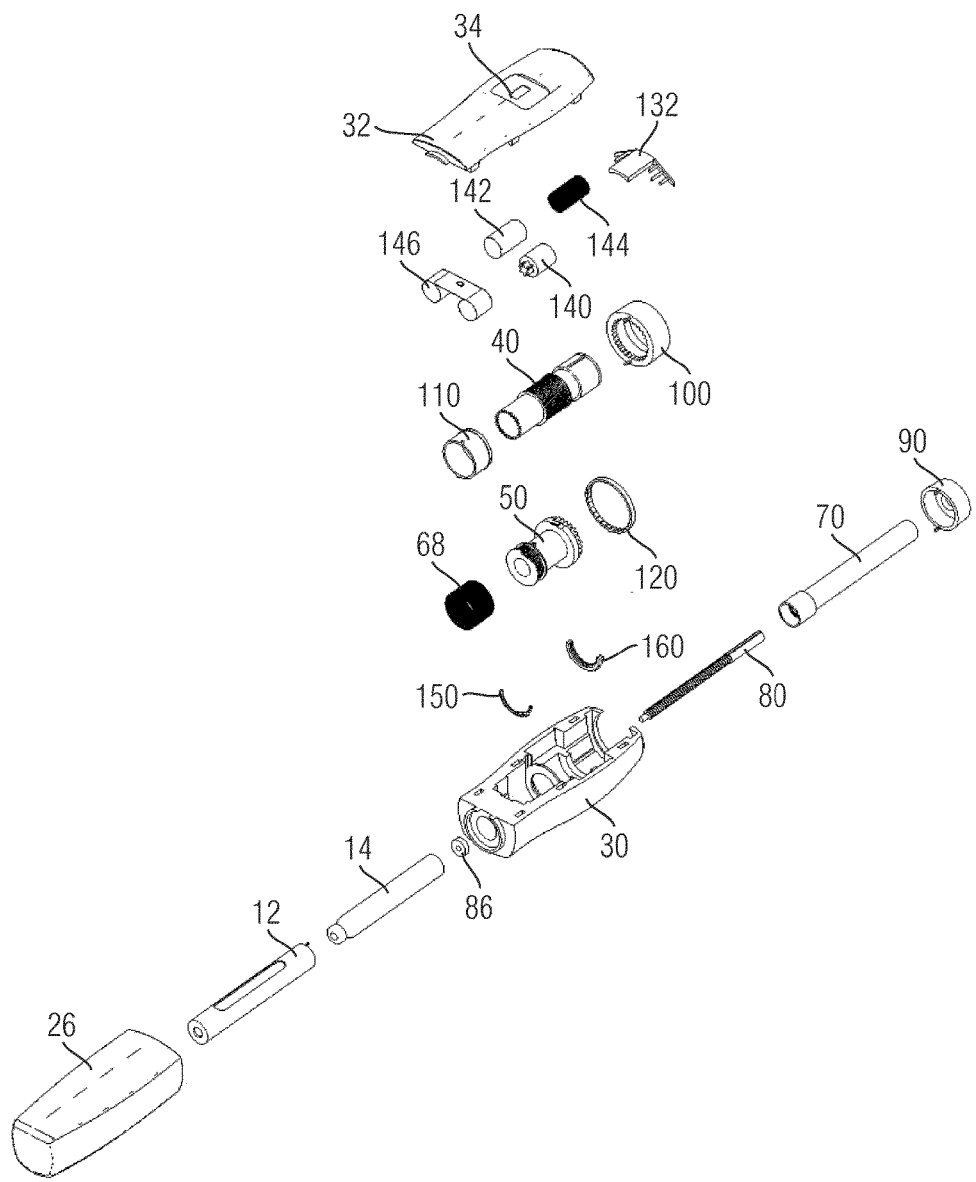
FIG. 10 shows an exploded view of the drug delivery device in perspective illustration.
Figure 26:
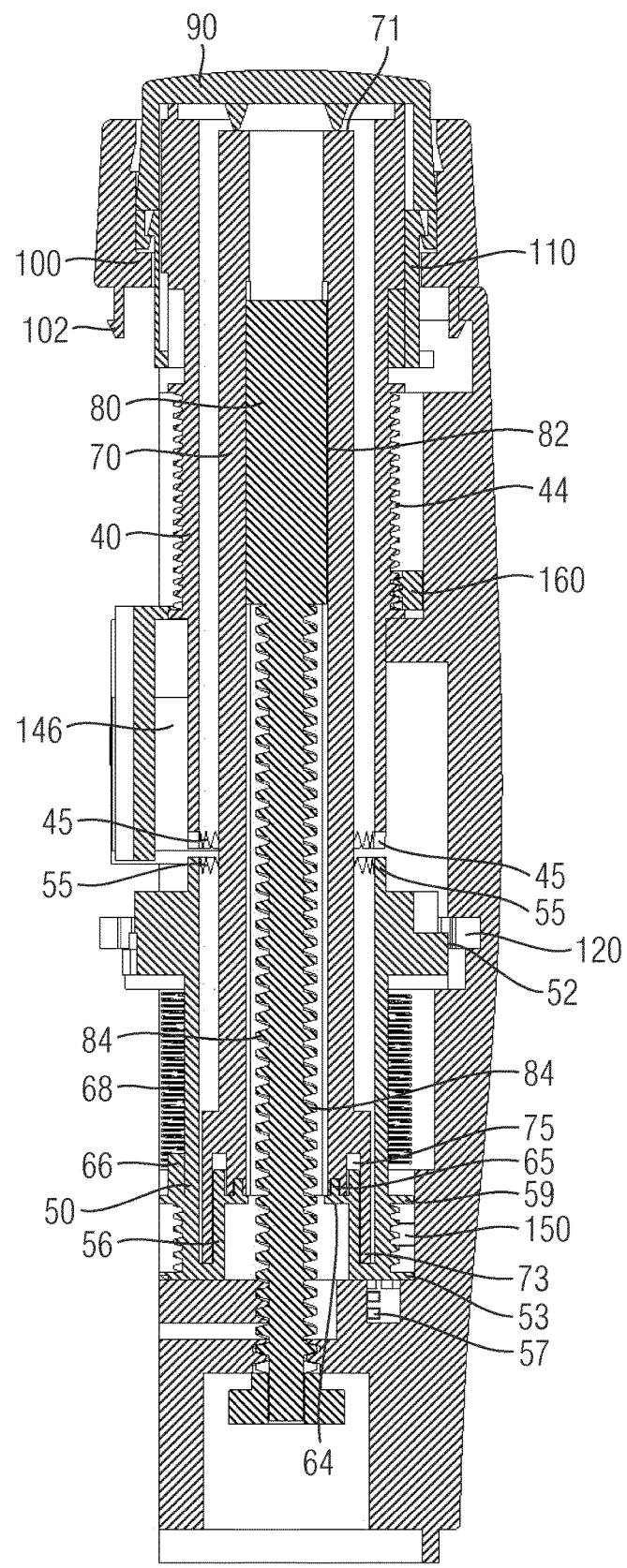

In FIGS. 1, 10 and 26 the drive mechanism 3 of a drug delivery device 10 is illustrated in an assembled and in an exploded view, respectively. The drug delivery device 10 is of pen-injector type and comprises a substantially cylindrical and axially elongated shape. Throughout the Figures the axial distal direction is denoted with reference number 1 and the opposite proximal direction is denoted with reference number 2. The drug delivery device 10 comprises a proximal housing component 30 to receive the drive mechanism 3.

In distal direction 1, the housing 30 is connected with a cartridge holder 12 which is adapted to accommodate and to receive a cartridge 14 containing the medicament to be dispensed by the drug delivery device 10. The cartridge 14 typically comprises a vitreous barrel 18 of cylindrical shape which is sealed in distal direction 1 by a pierceable sealing member, such like a septum.

In proximal direction 2, the cartridge 14 is sealed by a piston 16 slidably arranged in the vitreous barrel 18 of the cartridge 14. Displacement of the piston 16 in distal direction 1 leads to a respective built-up of a fluid pressure inside the cartridge 14. When the distal outlet of a cartridge 14 is connected with e.g. a needle assembly 20, as shown in FIG. 1, a predefined amount of the liquid medicament contained in the cartridge 14 can be expelled and dispensed via an injection needle 22 of the needle assembly 20.

In FIG. 1 however, a needle cap 24 to protect the double-tipped injection needle 22 is indicated. The needle assembly 20 is typically arranged on a distal end portion of the cartridge holder 12. Typically, a distally located socket of the cartridge holder 12 and the needle assembly 20 comprise mutually corresponding threads to screw the needle assembly 20 onto the cartridge holder 12 in a releasable and removable way.

Figure 2:
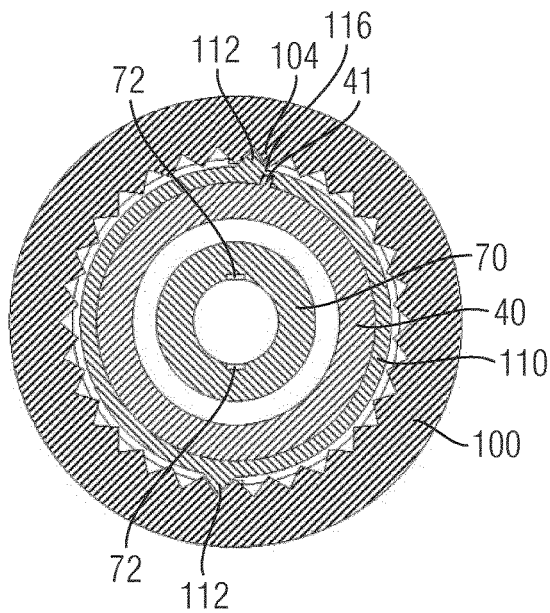
FIG. 2 shows a cross section along A-A according to FIG. 1.
Figure 3:
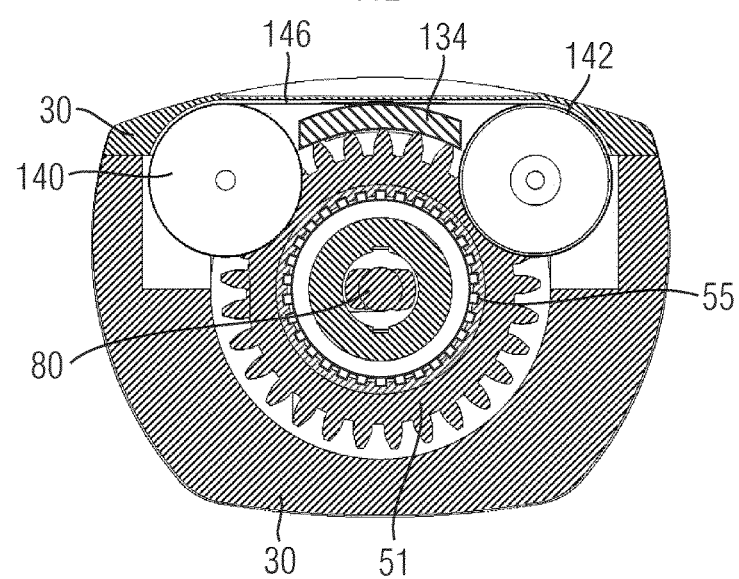
FIG. 3 shows a cross-section along B-B according to FIG. 1.

The cartridge holder 12 and hence the cartridge 14 is to be protected and covered by a protective cap 26 which is shown in FIGS. 2 and 3. Prior to setting and/or dispensing of a dose, the protective cap 26 as well as the inner needle cap 24 are to be removed. After dispensing or injecting of the medicament into biological tissue, the needle assembly 20 is typically to be discarded and the distal end of the drug delivery device 10 is to be covered by the protective cap 26.

The drive mechanism 3 as illustrated in an exploded view in FIG. 10 and as shown in cross section in its fully assembled configuration in FIGS. 1 and 26 comprises numerous functional components by way of which a dose of variable size can be set and subsequently dispensed.

The dose dispensing procedure comes along with a distally directed advancing displacement of the piston rod 80 relative to the housing 30. The drive mechanism 3 therefore comprises at least a housing 30, a piston rod 80 a drive sleeve 50 and a dispensing sleeve 70 which can be selectively and operably coupled for setting and dispensing of a dose respectively.

The dose dispensing procedure comes along with a distally-directed advancing displacement of a piston rod 80 relative to the housing 30. As illustrated for instance in FIGS. 1 and 26, the piston rod 80 comprises an outer threaded portion 84 at a distal end which is threadedly engaged with a radially centrally located and threaded support 31 of the housing. Advancing of the piston rod 80 in distal direction may therefore be achieved by a rotational movement of the piston rod 80 relative to the housing 30.

In the following, setting of a dose is described.

For setting of a dose, a user takes the drug delivery device 10 and starts to rotate the proximally located dose dial button 100 relative to the housing 30. The dose dial button 100 is of sleeve-like shape and is axially fixed to a proximal end of the housing 30 by way of axially extending and radially outwardly biased latch elements 102. As for instance indicated in FIG. 23, the latch elements 102 engage with a radially inwardly extending flange portion 38 provided at the distal end face of the housing 30.

Figure 23:
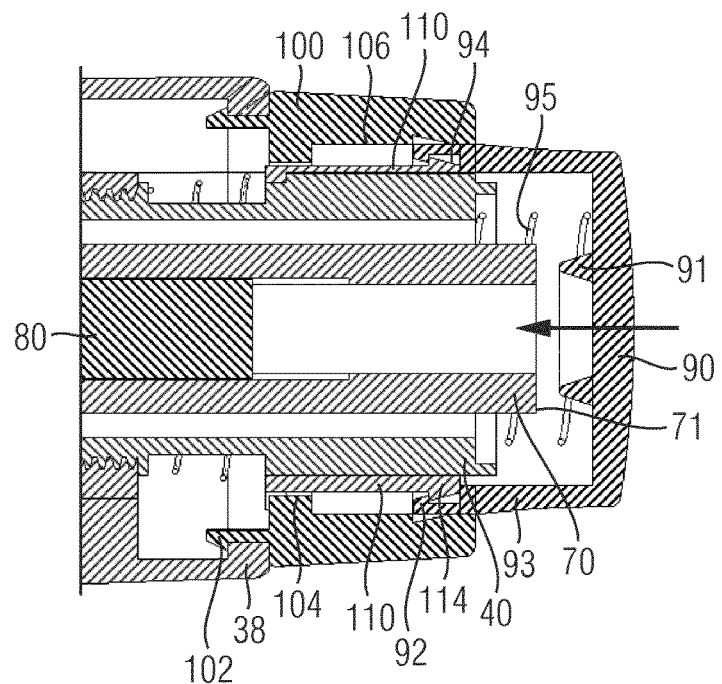
FIG. 23 shows an enlarged longitudinal cut through the proximal end of the drive mechanism.
Figure 24:
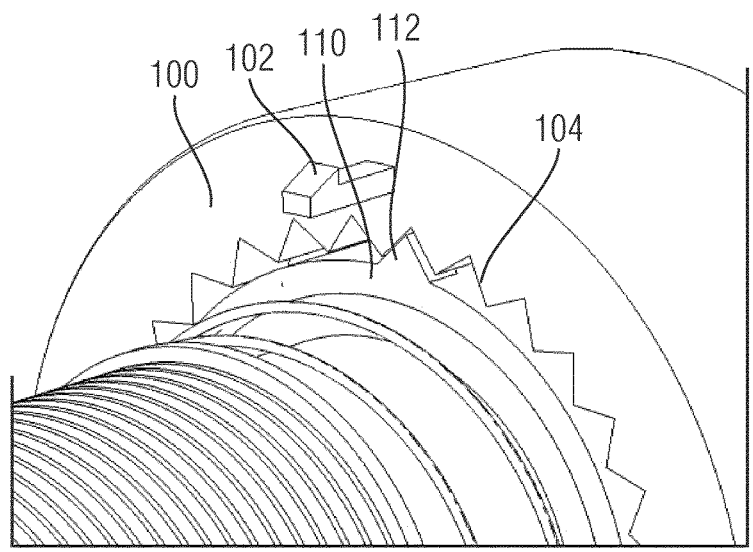
FIG. 24 is a perspective view of the mutual engagement of the dose setting clutch with the dose dial button.

As further shown in FIG. 23 the dose dial button 100 also axially abuts against the proximal end face of the housing 30, hence against the flange portion 38 so that the dose dial button 100 is axially fixed with respect to the housing 30. The mutual engagement of the dose dial button 100 and the housing 30 allows for a free rotation of the dose dial button 100 relative to the housing 30.

As shown in cross-section of FIG. 2 and FIG. 23, the dose dial button 100 comprises a toothed section 104 protruding radially inwardly from an inside facing sidewall portion 106 of the dose dial button 100.

As shown in FIG. 2, there is provided a dose setting clutch 110 inside the dose dial button 100. The sleeve-like dose setting clutch 110 comprises two radially outwardly extending teeth 112 that engage with the toothed section 104 of the dose dial button 100. Hence, a dose setting rotation of the dose dial button 100 leads to a corresponding rotation of the dose setting clutch 110. Moreover, the dose setting clutch 110 receives and is engaged with a dose setting sleeve 40 extending therethrough in axial direction.

In particular, the dose setting sleeve 40 is splined with the dose setting clutch. As shown in FIG. 2, the dose setting sleeve 40 comprises one radially outwardly extending protrusion 41 extending into an axially extending recess 116 provided at the inside of the dose setting clutch 110. Therefore, a rotation of the dose dial button 100 not only rotates the dose setting clutch 110 but also the dose setting sleeve 40.

As illustrated in the longitudinal cross-sections of FIG. 1 and FIG. 26, the dose setting sleeve 40 extends axially inwardly into the housing 30 of the drive mechanism 3 and engages with a drive sleeve 50 by means of mutually corresponding crown wheel portions 45, 55. As indicated in FIG. 1, a crown wheel portion 45 provided at a distal end face of the dose setting sleeve 40 engages with a correspondingly crown wheel portion 55 provided at a proximal end face of the drive sleeve 50. In this way, and at least in dose setting mode, dose setting sleeve 40 and drive sleeve 50 are rotatably engaged. Hence, a dose setting rotation of the dose setting sleeve 40 equally transfers to a corresponding rotation of the drive sleeve 50.

Figure 4:
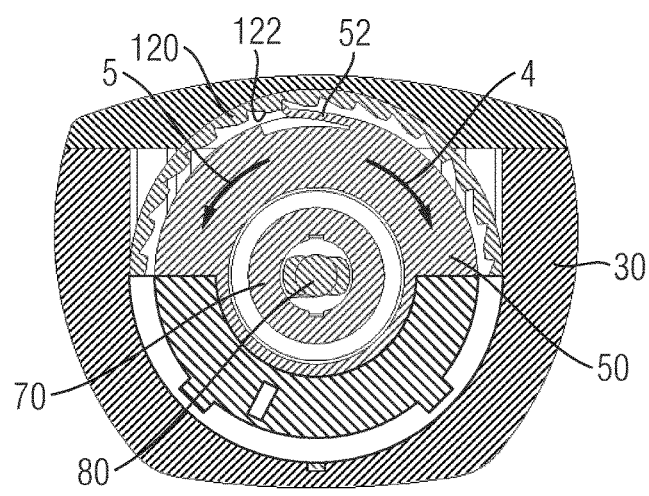
FIG. 4 shows a cross-section along C-C according to FIG. 1.
Figure 5:
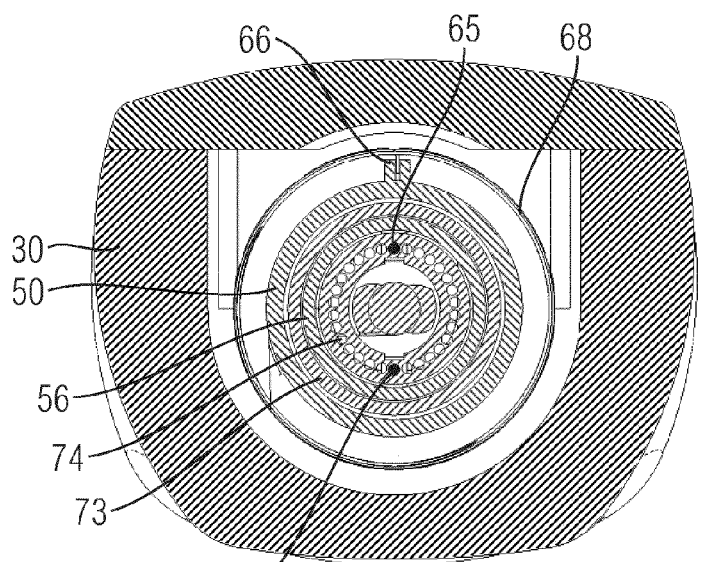
FIG. 5 is indicative of a cross-section along D-D according to FIG. 1.

The drive sleeve 50 is biased with respect to the housing 30 by means of a helical spring 68. As indicated in FIG. 5, 14 and in FIG. 26 the drive sleeve 50 comprises a radially outwardly extending mount 66 to receive one end of the helical spring 68, which axially and circumferentially extends around a cylindrical portion of the drive sleeve 50. An opposite end of the helical spring 68 is fastened to the housing 30. In this way, rotation of the drive sleeve 50 in a dose setting direction 4 as illustrated in FIG. 4 will typically occur against the action of the helical spring 68.

The drive sleeve 50 further comprises a radially outwardly extending ratchet member 52 which is engaged with a toothed inner surface 122 of a toothed ring 120 when in dose setting mode. The toothed ring 120 is fastened and fixed in the housing 30. The ratchet member 52 is arc-shaped and is therefore resiliently deformable in radial direction. It may further comprise a radially outwardly extending tooth or nose that mates with the correspondingly shaped toothed inner surface 122 of the toothed ring 120. As indicated in cross-section according to FIG. 4, the ratchet member 52 meshes with the toothed inner surface 122 when rotated clockwise, e.g. in dose setting direction 4. Passing of the ratchet member 52 along the consecutive teeth of the toothed inner surface 122 generates an audible feedback to the user, thereby indicating, that the dose is step-wise incremented.

The geometry of the toothed surface 122 of the toothed ring 120 and the free end of the ratchet member 52 is designed such, that the spring force arising from the helical spring 68 and acting in opposite, hence dose dispensing direction 5 is not large enough to rotate the drive sleeve 50 in the dose dispensing direction 5. In this way, mechanical energy can be stored by and in the helical spring 68 which is to be released only on demand during a subsequent dose dispensing procedure. For dispensing of a dose the mutual engagement of the ratchet member 52 and the toothed inner surface 122 is released.

Moreover, the toothed inner surface 122 and the ratchet member 52 of the drive sleeve 50 engage in such a way, that a dose decrementing rotation of the drive sleeve 50 is indeed possible, e.g., when a user exerts a respective counter-directed angular momentum to the dose dial button 100, which exceeds the resilient resistance provided by the mutual engagement of ratchet member 52 and toothed inner surface 122.

Figure 12:
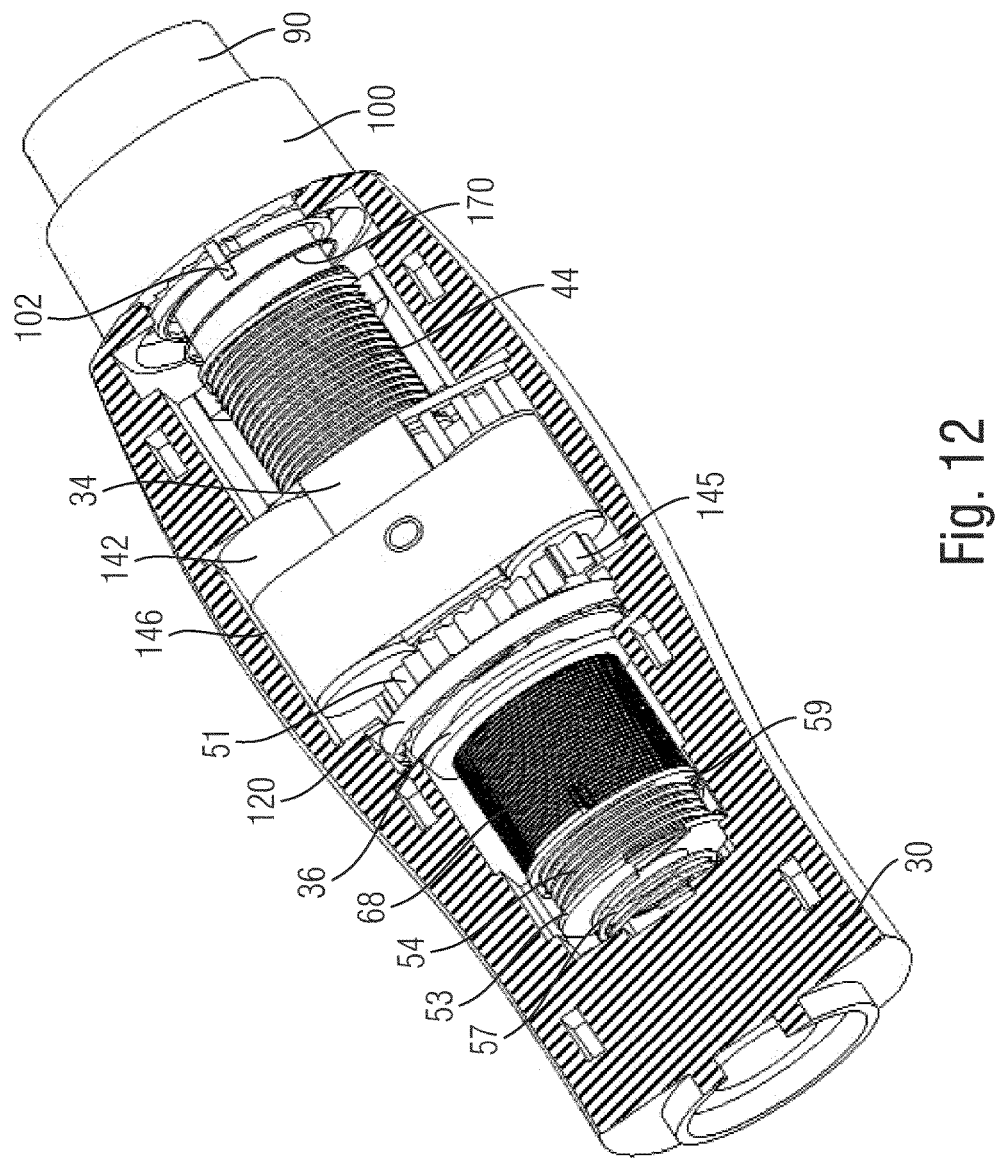
FIG. 12 shows the drive mechanism according to FIG. 11 assembled in the housing.
Figure 13:
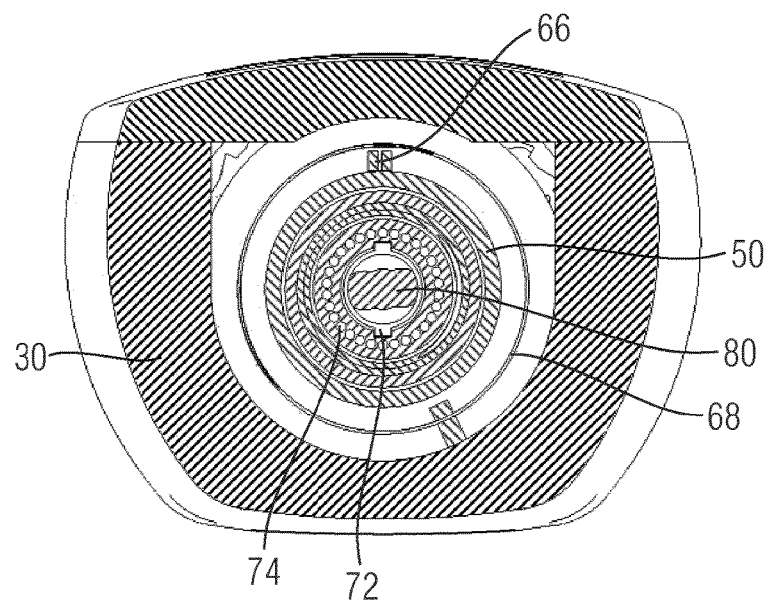
FIG. 13 is illustrative of a cross-section along I-I according to FIG. 1.
Figure 15:
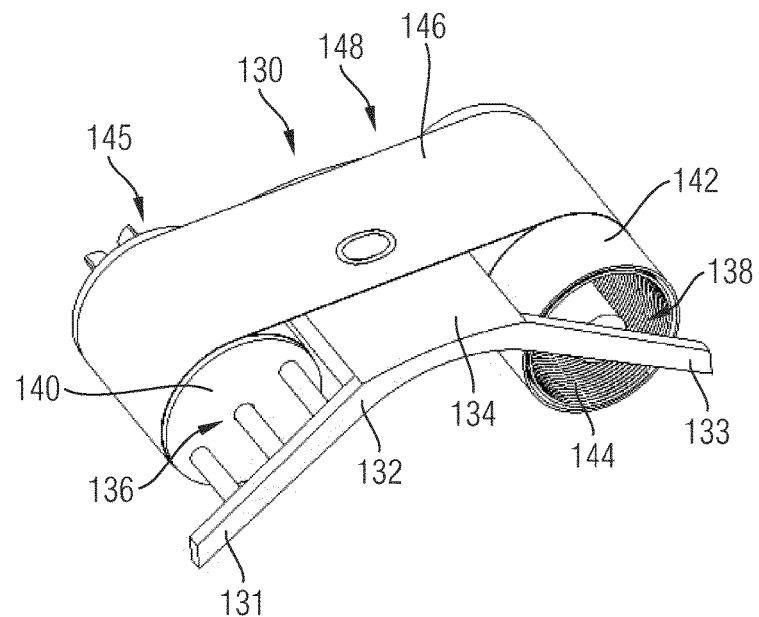
FIG. 15 shows a perspective illustration of the dose indicating mechanism.
Figure 16:
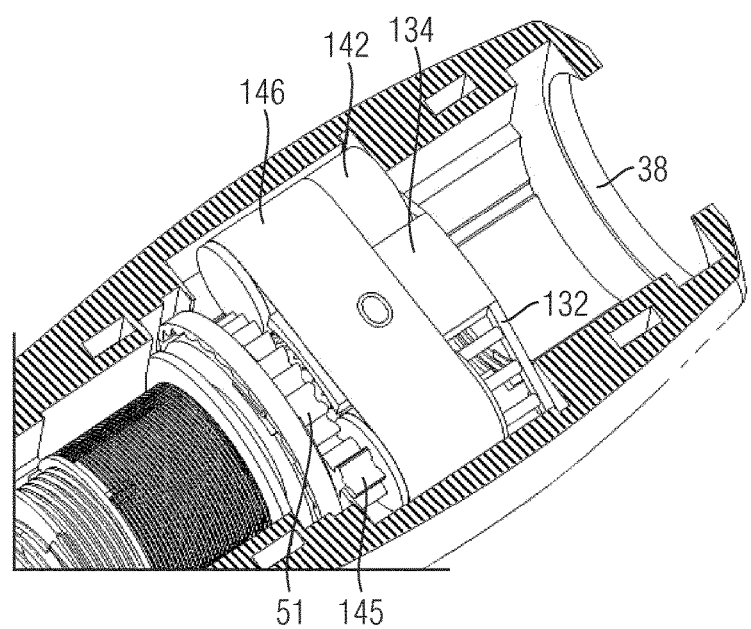
FIG. 16 shows the dose indicating mechanism assembled in the housing and interacting with the drive sleeve.

The drive sleeve 50 further comprises a gear wheel 51 or a respective geared section axially adjacent to the toothed ring 120. As shown in FIGS. 12 and 16, the gear wheel 51 meshes with a corresponding gear wheel 145 of a first spool 140 of a dose indicating mechanism 130 which is separately illustrated in FIG. 15. The dose indicating mechanism 130 comprises a base 130 featuring a support section 134 and two laterally extending branches 131 and 133. On each of said branches 131, 133 a bearing 136, 138 for a first spool 140 and for a second spool 142 is provided, respectively. As shown in FIG. 15, the first spool is rotatably supported by the bearing 136 on the branch 131 while the second spool is arranged on the second branch 133 by the bearing 138.

The two spools 140, 142 are further interconnected by means of a dose indicating tape 146. In an initial configuration, the dose indicating tape featuring a sequence of dose indicating numbers 148 is almost completely coiled up on the second spool 142. A free end of said tape 146 is connected and attached to the outer circumference of the first spool 140. Due to the geared interaction of drive sleeve 50 and first spool 140, rotation of the drive sleeve 50 during a dose setting procedure comes along with a corresponding rotation of the first spool 140, thereby coiling up at least a portion of the dose indicating tape 146 onto the first spool 140.

As it is further indicated in FIGS. 10 and 15, an unwinding rotation of the second spool 142 will only occur against the action of a spool spring 144, which comprises a helical spring element 144 located inside the spool 142. By means of such a spool spring 144, the dose indicating tape 146 can be strained in order to reduce a potential slack between the two spools 140, 142 to a minimum. Moreover, by means of the helical or torsion spool spring 144, the entire dose indicating mechanism 130 can be pre-stressed during pre-assembly of the device.

The dose indicating mechanism 130 can be assembled in its entirety into the housing 30 as indicated in FIG. 16. Depending on the degree of rotation of the drive sleeve 50 during a dose setting procedure, the dose indicating tape 146 will be wound up to the first spool 140. Above the support section 134 of the base 132 a respective number 148 representing the size of the said dose will show up. In its fully assembled configuration, the dose indicating mechanism 130 will be covered by a closure 32 of the housing 30 as indicated in FIG. 10.

Said closure 32 comprises a dose indicating window 34, through which a comparatively large number 148 provided on the dose indicating tape 146 is clearly visible. By means of the winding mechanism provided by the dose indicating mechanism 130 the numbers 148 can be printed and displayed comparatively large in order to allow a good and sufficient legibility of the size of the said dose. When appropriately mounted to the housing 30 the closure 32 typically flushes with the outer side wall of the adjacent housing. Hence, the closure 32 forms part of the housing 30 and is effectively integrated therein.

During a dose dispensing operation, which will be explained in greater detail below, the drive sleeve 50 is allowed to rotate in the opposite, hence in the dose dispensing direction 5. Also in the dose dispensing mode, the drive sleeve 50 stays geared with the gear wheel 145 of the first spool 140. Under the action of the spool spring 144, the tape 146 will then return and will coil up on the second spool 142. Correspondingly the numbers showing up in the dose indicating window will successively count down.

Figure 6:
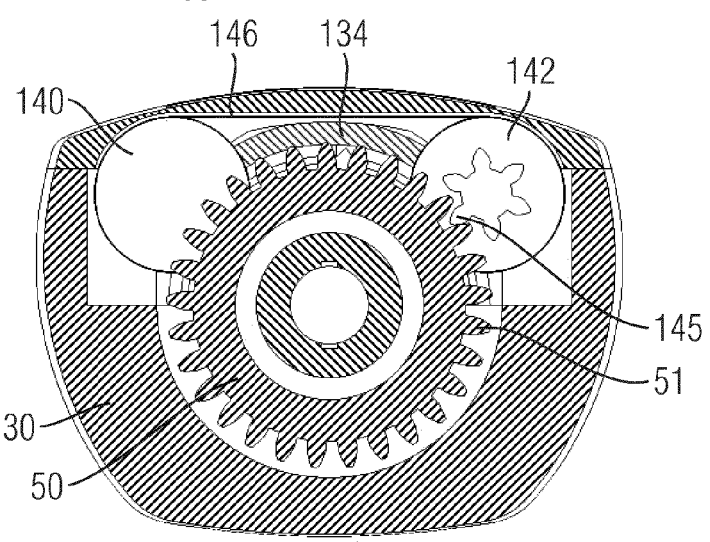
FIG. 6 shows a cross-section along E-E according to FIG. 1.

In the cross-section of FIGS. 3 and 6, the geared engagement of the drive sleeve 50 with the first spool 140 is not explicitly illustrated. However, from the FIG. 16 the permanent geared interaction of the drive sleeve 50 with the first spool 140 is clearly visible.

In the following, dispensing of a dose is described.

The drive mechanism 3 further comprises a dispensing sleeve 70 and an injection button 90. The dispensing sleeve 70 extends almost through the entire drive mechanism 3 in axial direction while the cup-shaped injection button 90 is located at a proximal end of the drive mechanism 3, hence at a proximal end of the entire drug delivery device 10. The injection button 90 is axially secured to the housing 30 by means of an axially and radially inwardly extending latch element 92 adapted to engage with a correspondingly shaped latch element 114 provided at a proximal end of the dose setting clutch 110.

The latch element 92 of the injection button 90 extends axially inwardly and protrudes from a radially inwardly extending latch 94, which may form a distal end section of the sidewall portion 93 of the injection button 90. The injection button 90 is operable to be depressed in distal direction as indicated in FIG. 23. In a central portion of its proximal end face the injection button 90 may comprise an integrated spring, e.g. an injection spring 91 which engages with a proximal end face of the dispensing sleeve 70.

Distally-directed depression of the injection button 90 therefore induces a corresponding distally-directed displacement of the dispensing sleeve 70. At the same time, the dose setting clutch 110 is displaced in distal direction so that its radially outwardly extending teeth 112 disengage from the toothed section 104 of the dose dial button 100. In this way, the dose dial button 100 can be decoupled from the dose setting clutch 110 and accordingly from the dose setting sleeve 40. Any further rotation of the dose dial button 100 during a dose dispensing procedure is therefore substantially effectless and will not lead to a further rotation of the dose setting sleeve 40.

Distally-directed displacement of the dispensing sleeve 70 acts against the action of at least one spring element 57, 58. Moreover, as illustrated in the longitudinal cross-sections of FIGS. 1 and 26 the distal end section of the dispensing sleeve 70 axially abuts and axially engages with the drive sleeve 50. This way, an axially and distally directed displacement of the dispensing sleeve 70 can be transferred to a respective distally-directed displacement of the drive sleeve 50.

While the drive sleeve 50 is in a proximal dose setting position during a dose setting mode of the drive mechanism 3 it can now be pushed or slaved into a distal dose dispensing position. The drive sleeve 50 is supported in axial direction relative to the housing 30 by means of a distally located drive sleeve spring element 57, which may axially abut against the threaded support 31 of the housing 30. Additionally, there may be provided a further dispensing sleeve spring element 58 between the dispensing sleeve 70 and the drive sleeve 50.

As shown in cross-sections of FIGS. 1 and 26, the drive sleeve 50 comprises a radially inwardly extending inner sleeve portion 56 at its distal end, which is adapted to form an annular receptacle to receive a correspondingly shaped distally extending extension 73 of the dispensing sleeve 70. In this way, dispensing sleeve 70 and drive sleeve 50 can be secured and fixed with respect to each other in radial direction.

Moreover, the additional spring element 57, to be denoted as drive sleeve spring element 57, may be positioned in the interface formed by the dispensing sleeve 70 and the drive sleeve 50 in order to separate the dispensing sleeve from the drive sleeve as soon as the injection button 90 is no longer depressed.

The dispensing sleeve 70 further comprises a ring-shaped receptacle at a distal end to receive the free end of the proximally extending inner sleeve portion 56 of the drive sleeve 50. The receptacle 75 may be suitable to receive another spring element 58 to be denoted as dispensing sleeve spring element 58.

As further illustrated in FIG. 5 and FIG. 26, the drive sleeve 50 comprises a radially inwardly extending flange portion 64 protruding from the proximal end of the inner sleeve portion 56. On said flange portion 64 there are provided at least two axially and proximally extending pins 65 adapted to engage with a punched structure 74 provided at the distal end face of the dispensing sleeve 70. In this way, a torque transmitting engagement of dispensing sleeve 70 and drive sleeve 50 can be provided. A dose dispensing rotation of the drive sleeve 50 may then equally transfer to the dispensing sleeve 70.

The dispensing sleeve 70 is further rotatably locked with the piston rod 80. For this purpose, the dispensing sleeve 70 comprises an axially and radially extending recess 72 to receive at least one correspondingly shaped and radially outwardly extending protrusion 82 of the piston rod 80 as shown in cross-section in FIG. 8. With such a splined engagement, any rotative movement of the dispensing sleeve 70 can be equally transferred to a corresponding rotation of the piston rod.

Since at least a distal end of the piston rod 80 is provided with an outer thread 84 which is threadedly engaged with the threaded support 31 of the housing 30, any rotation of the dispensing sleeve 70 and a corresponding rotation of the piston rod 80 will lead to a distally-directed advancing of the piston rod 80 and its distally located pressure foot 86 relative to the housing 30 for driving the piston 16 of the cartridge 14 further into the barrel 18 of the cartridge 14, thereby expelling a predefined amount of the medicament contained in the cartridge 14.

Due to the splined and direct engagement of the dispensing sleeve 70 and the piston rod 80, any axially-directed displacement of the dispensing sleeve 70 relative to the piston rod 80 has no influence on the axial position of the piston rod 80.

Axially and distally-directed displacement of the dispensing sleeve 70 may be conducted in two consecutive steps. In a first step, the dispensing sleeve 70 is displaced in distal direction until a mutual and axial engagement with the drive sleeve 50 is attained. In such an intermediate position of the dispensing sleeve 70 the dispensing sleeve 70 rotatably engages with the drive sleeve 50 since the pins 65 of the drive sleeve engage and enter the punched structure 74 of the dispensing sleeve 70.

Figure 14:
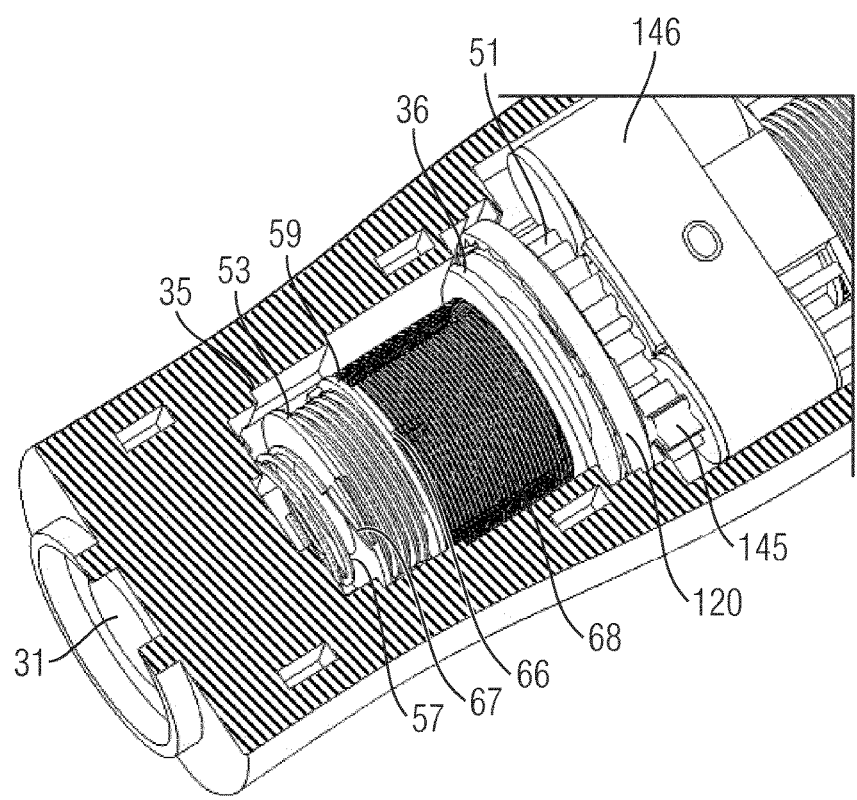
FIG. 14 shows the drive sleeve assembled in the housing in a perspective illustration.

In this intermediate configuration the drive sleeve 50 is still engaged with the toothed ring 120 and the drive sleeve 50 is still hindered to rotate relative to the housing 30. It is only due to a further distally-directed displacement of the dispensing sleeve 70, that the drive sleeve 50 is displaced in distal direction 1 against the action of the spring element 57. When reaching a distal stop configuration, in which for instance a distally located radially outwardly extending flange 53 of the drive sleeve 50 abuts with a radially inwardly extending ledge 35 of the housing 30 or in which the radially outwardly extending ratchet member 52 axially engages with the axial stop 36 of the housing 30, as indicated in FIG. 14, the combined distally directed motion of the dispensing sleeve 70 and the drive sleeve 50 can be stopped.

The two consecutively and sequentially depressable spring elements 57, 58 typically comprise different spring constants so that a rotative coupling of dispensing sleeve 70 and drive sleeve 50 can be established before the drive sleeve 50 and its ratchet member 52 is axially displaced from the toothed ring 120 such that the drive sleeve 50 may freely rotate under the action of the helical spring 68.

As further illustrated in FIG. 26, axial displacement of the drive sleeve 50 in distal direction 1 also decouples and releases the drive sleeve 50 from the dose setting sleeve 40. The dose setting sleeve 40 is axially fixed with respect to the housing 30. By the separation of the drive sleeve 50 from the dose setting sleeve 40 during a dose dispensing procedure, the dose setting sleeve 40 never rotates in the dose dispensing direction 5 but always incrementally rotates in the opposite dose setting direction 4.

Figure 9:
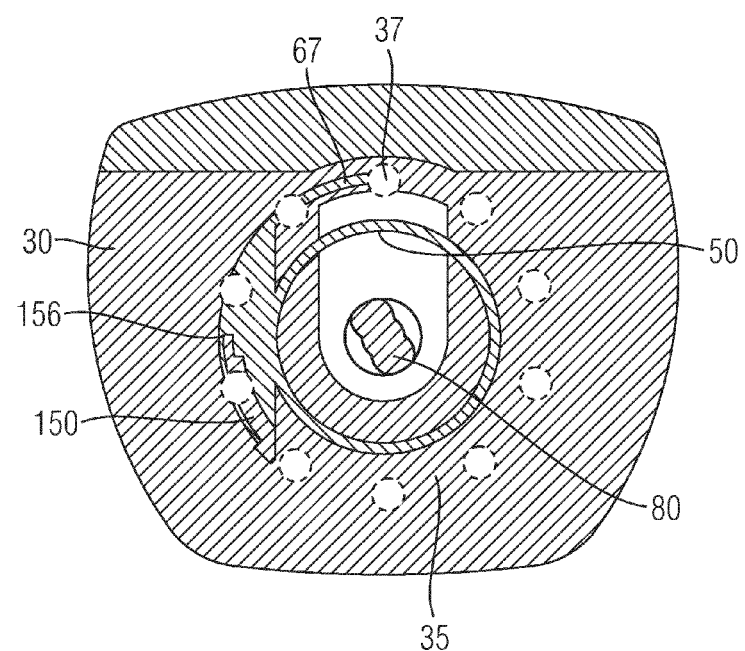
FIG. 9 shows a cross-section along H-H according to FIG. 1.
Figure 25:
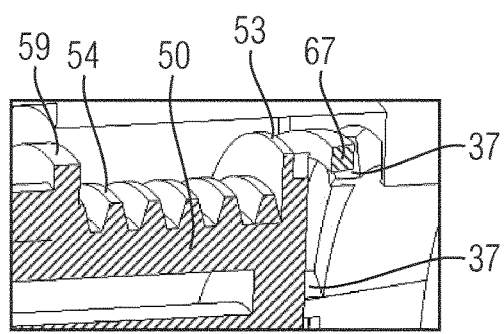
FIG. 25 shows a distally located clicking member of the drive sleeve engaging with the housing and FIG. 26 shows an enlarged longitudinal cut through the drive mechanism.

The drive sleeve 50 further comprises an arc-shaped clicking member 67 extending in distal direction 1 from the distal flange portion 53 of the drive sleeve 50. As indicated in FIG. 25, and when rotating during dose dispensing the clicking member 67 consecutively engages with feedback element 37, which may be provided in form of axially extending protrusions or recesses on a ledge 35 of the housing 30. As indicated in the cross-section according to FIG. 9 numerous feedback elements 37 are arranged around the ledge 35 of the housing 30. When the drive sleeve 50 revolves under the action of the spring 68, the clicking member 67 generates a frequently repeating clicking sound which is audible by the patient or user of the device 10, thereby indicating to the user, that a dispensing action is actually in progress.

The dose dispensing procedure requires that the injection button 90 is permanently depressed in distal direction against the action of the injection spring 91 as well as against the action of the spring elements 57, 58. A premature release of the injection button 90 will sequentially lead to a proximally-directed displacement of the drive sleeve 50 into its dose setting position, in which the ratchet member 52 re-engages with the toothed ring 120, thereby rotatably interlocking the drive sleeve 50 to the housing 30.

Figure 11:
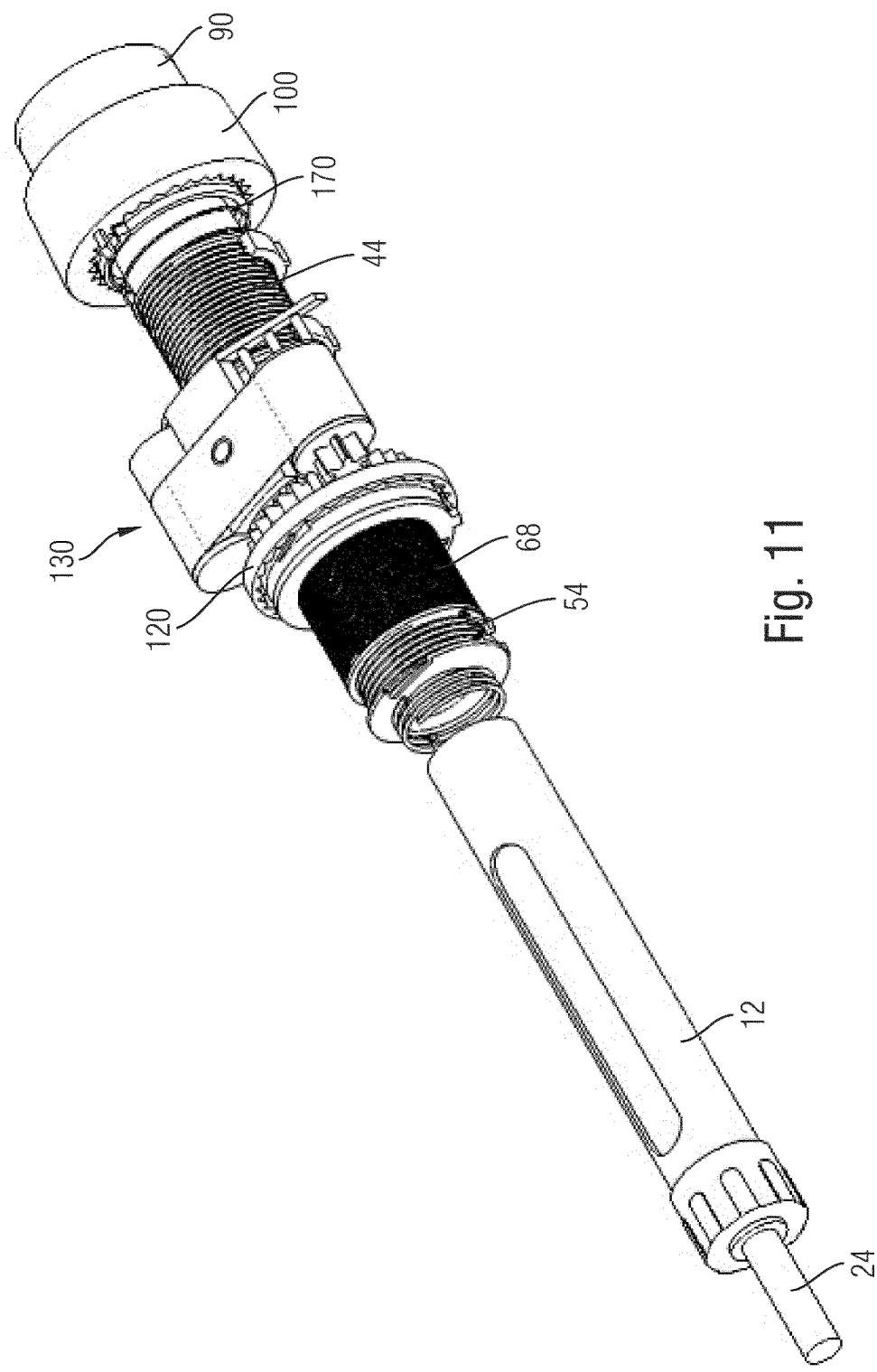
FIG. 11 shows a perspective view of the drive mechanism without the surrounding housing.

At the same time also a rotative engagement of the dose setting sleeve 40 and the drive sleeve 50 is re-established. Finally also the dose setting clutch 110 will return into its initial configuration as shown in FIG. 23. This may either occur under the action of an additional spring element 170 as shown in FIGS. 11 and 12. Alternatively, a proximally-directed displacement of the dose setting clutch 110 may be governed by the mutual engagement of the latch members 92 and 114 of the injection button 90 and the dose setting clutch 110, respectively.

Figure 8:
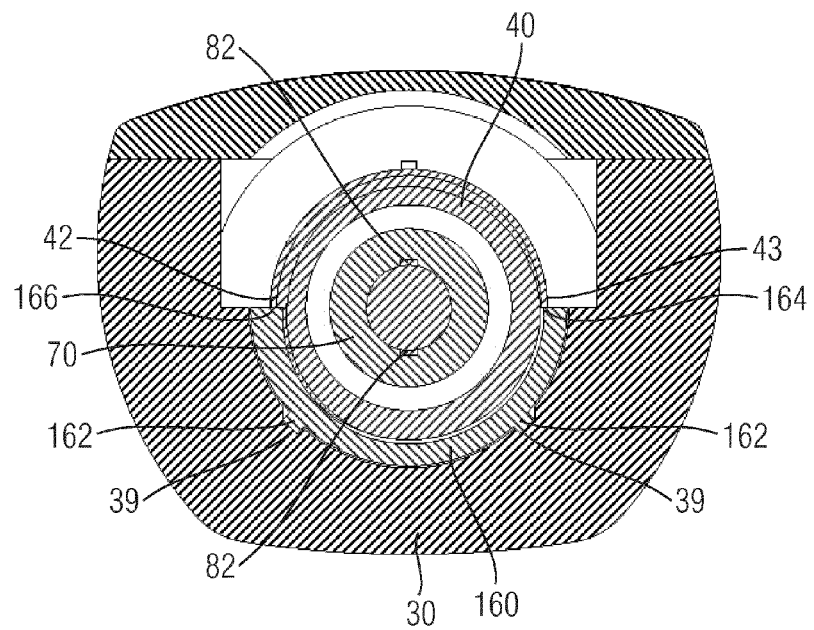
FIG. 8 shows a cross-section along G-G according to FIG. 1

In order to provide an end of content mechanism the dose setting sleeve 40 comprises a threaded portion 44 at its outer circumference. Said threaded portion 44 is engaged with a last dose limiting member 160 comprising a corresponding thread on its inside facing portion. The last dose limiting member 160 is arc-shaped as illustrated in FIG. 8 and it is radially sandwiched between the outer circumference of the threaded portion 44 of the dose setting sleeve 40 and an inside facing sidewall portion of the housing 30.

The last dose limiting member 160 is threadedly engaged with the dose setting sleeve 40 but is allowed to axially slide along the housing 30. The last dose limiting member 160 is further rotatably locked to the housing 30. For this purpose, the housing comprises axially and radially outwardly extending recesses 39 on its inside facing side wall portion to receive correspondingly shaped radially outwardly extending protrusions 162 of the last dose limiting member 160.

During a dose setting procedure the dose setting sleeve 40 rotates relative to the housing which leads to a respective axial displacement of the last dose limiting member 160. Accordingly, with consecutive dose setting procedures the last dose limiting member 160 travels step-by-step along the recesses 39 of the housing 30. Since the dose setting sleeve 40 is exclusively rotated during dose incrementing or dose decrementing, the axial position of the last dose limiting member 160 relative to the dose setting sleeve 40 is directly indicative of the total amount of doses set and dispensed by the drive mechanism 3 during consecutive dose setting and dose dispensing procedures.

The threaded portion 44 of the dose setting sleeve 40 further comprises a distally located radial stop 42 which is adapted to engage with a stop face 166 of the last dose limiting member 160. In a final assembly configuration, the axially and radially extending stop face 166 is brought in abutment with the radial stop 42, thereby representing a zero dose stop configuration. This way, a dose decrementing rotation of the dose setting sleeve 40 can be effectively prevented.

The opposite circumferential end of the last dose limiting member 160 provides a comparable stop face 164 which his adapted to engage with a radial stop 43 provided at the opposite end of the threaded portion 44 of the dose setting sleeve 40. This stop configuration serves as an end of content stop and prevents a further rotation of the dose setting sleeve when the accumulated amount of medicament already set would otherwise exceed the amount of medicament left in the cartridge 14.

Figure 21:
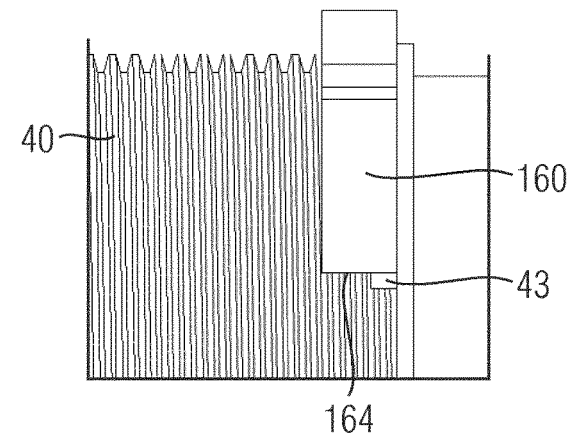
FIG. 21 shows a side view of the last dose limiting member engaging with a last dose stop of the dose setting sleeve and FIG. 22 is a perspective illustration of the last dose limiting member threadedly engaged with a threaded portion of the dose setting sleeve.
Figure 22:
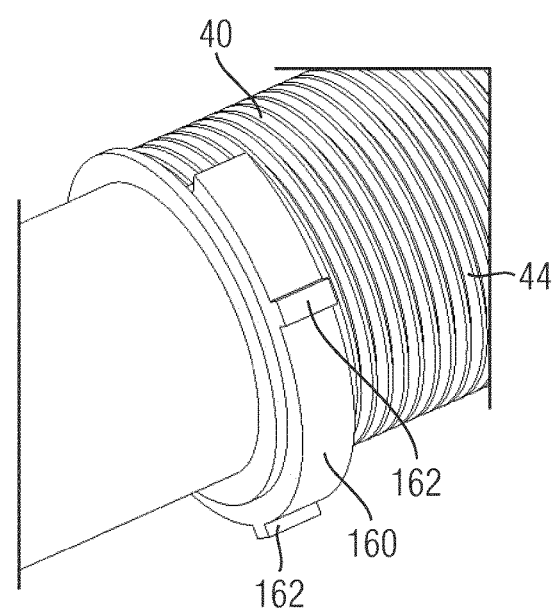

The last dose limiting configuration as for instance illustrated in FIG. 21 may correspond to a maximum size of a cartridge 14 of e.g. 450 I.U.

In other embodiments, also an inside facing portion of the housing 30 could provide a corresponding stop to engage with the last dose limiting member 160.

Figure 7:
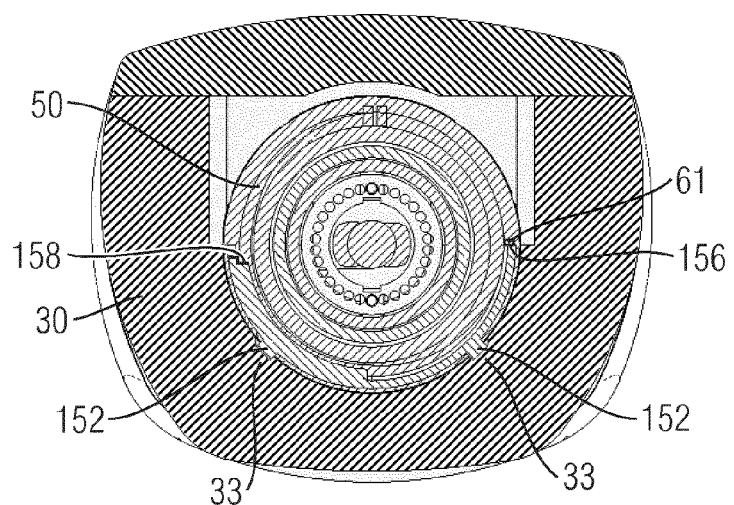
FIG. 7 shows a cross-section along F-F according to FIG. 1.
Figure 18:
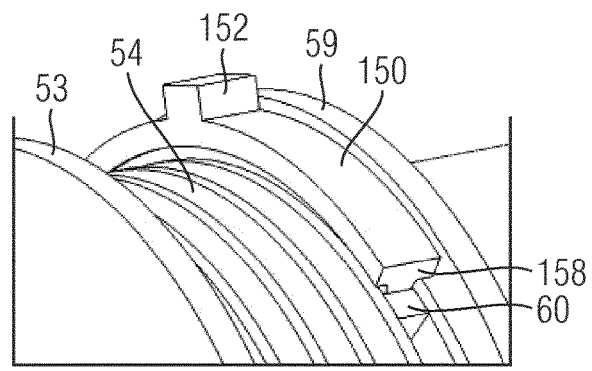
FIG. 18 shows a perspective illustration of the single dose limiting member in a different stop configuration on a threaded portion of the drive sleeve.

In a rather similar way also the drive sleeve 50 comprises a threaded portion 54 extending between a distal flange portion 53 and a proximal flange portion 59 as illustrated in FIGS. 14 and 18. The threaded portion 54 is threadedly engaged with a single dose limiting member 150, which is also of arc-shape and which comprises radially outwardly extending protrusions 152 to engage with correspondingly shaped radially outwardly and axially extending recesses or grooves 33 of the housing 30, as illustrated in FIG. 7.

This way, a rotation of the drive sleeve 50 in the dose setting direction 4 comes along with an axial displacement of the single dose limiting member 150 along the threaded portion 54 of the drive sleeve 50. In a zero dose configuration as illustrated in detail in FIGS. 17 and 19 a stop face 154 and a circumferential end of the single dose limiting member 150 is in abutment with a radially extending stop 61 provided on the distal flange 53.

Since the single dose limiting member 150 is threadedly engaged with the drive sleeve 50 and since the single dose limiting member 150 is rotatably locked to the housing 30, the engagement of the stop face 154 with the radial stop 61 inhibits a rotation of the drive sleeve 50 in the dose dispensing direction 5. In the opposite circumferential direction, the arc-shaped single dose limiting member 150 comprises another stop face 158 which is adapted to engage with another radial stop 60 provided in or on the outer threaded portion 54 of the drive sleeve 60.

The radial stop 60 is provided near a proximal flange portion 59 of the drive sleeve 50 as shown in FIG. 18. The mutual engagement of the stop face 158 with the radial stop 60 serves to limit a maximum dose to be set during a dose setting procedure. Since the single dose limiting member 150 is rotatably locked to the housing 30, the drive sleeve 50 is hindered to rotate any further when the radial stop 60 engages with the stop face 158. The configuration as illustrated in FIG. 18 may therefore correspond to a maximum single dose size of e.g. 120 I.U.

Since the drive sleeve 50 rotates in dose setting direction 4 during dose setting and in a dose dispensing direction 5 during dose correction or dose decrementing as well as during dose dispensing, the single dose limiting member 150 will always return into the zero dose configuration at the end of a dose dispensing procedure. In order to generate an audible signal, that the end of a dose injection has reached, the single dose limiting member 150 is further equipped with a circumferentially extending or tangentially extending clicking member 156, which is resiliently deformable in axial direction.

Figure 17:
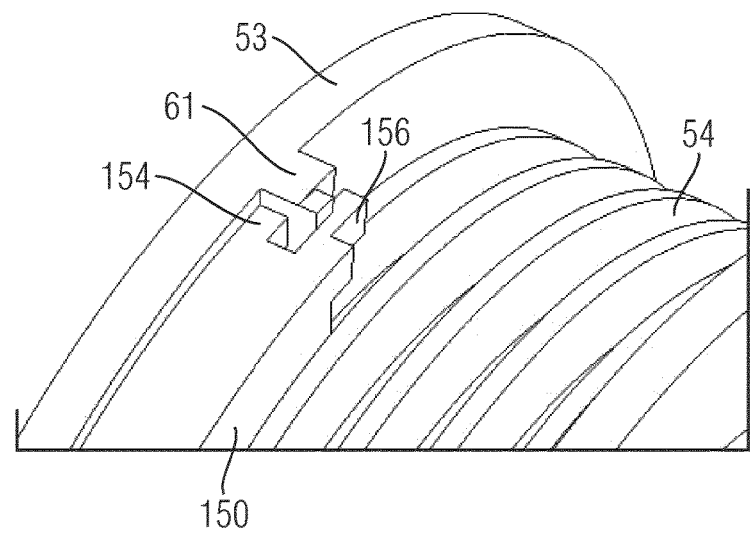
FIG. 17 is illustrative of an enlarged view of the single dose limiting member engaged with a radial stop of the drive sleeve.
Figure 19:
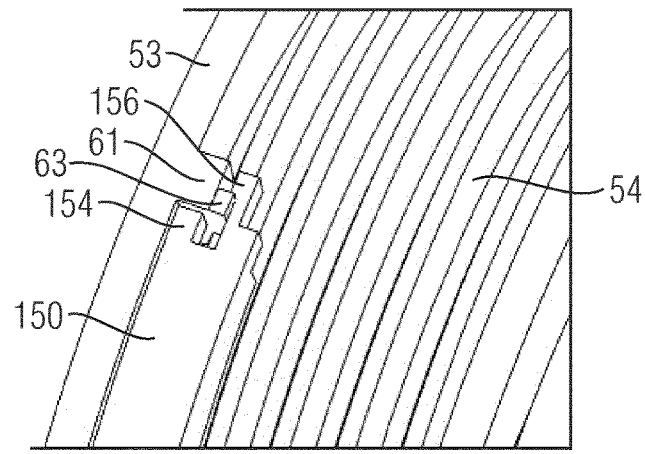
FIG. 19 shows an enlarged view of the configuration according to FIG. 17.
Figure 20:
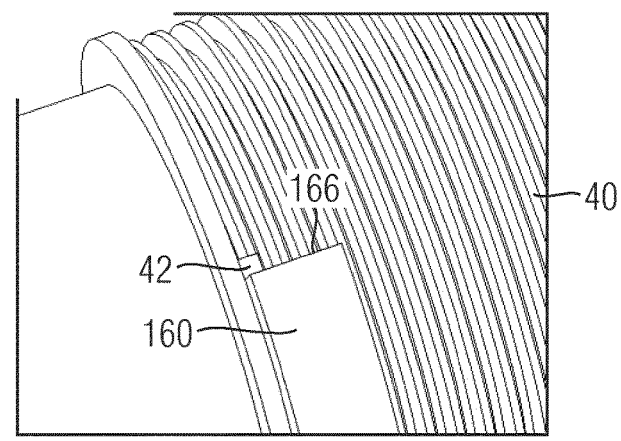
FIG. 20 is a side view of the last dose limiting member engaging with a radial stop of the dose setting sleeve.

The clicking member 156 provides a kind of a releasable latch which engages with a protrusion 63 axially extending from the radial stop 61 of the drive sleeve. The protrusion 63 and the clicking member 156 are shaped and configured such, that an audible click sound is generated when the zero dose configuration as shown in FIGS. 17 and 19 is reached.

The zero dose stop, hence the radial stop 42 of the drive sleeve 40 may be implemented only optionally since the single dose limiting member 150 provides a zero-dose stop functionality.

Generally, with all threaded engagements of the last dose limiting member 160 and the single dose limiting member 150 with the dose setting sleeve 40 or with the drive sleeve 50 the last thread of threaded sleeves 40, 50 in close or direct vicinity of a respective stop 42, 43 or 60, 61 could feature an increased lead in order to allow for an increase of the size of the radial extension of the respective stops. In this way the stop 42, 43, 60, 61 would be provided with an increased mechanical stability thus allowing to improve the performance of the respective stop.

Alternative to the radially extending stops 42, 43, 60, 61 it is generally conceivable to implement axially acting stops with respective radially and circumferentially extending stop faces. But since axial stops 42, 43, 60, 61 featuring radially and axially extending stop faces, exhibit a well-defined and more precise stopping behaviour when engaging with respective stop faces of the single- and/or last dose limiting members 150, 160 use of radially extending stops 42, 43, 60, 61 may be of advantage.

LIST OF REFERENCE NUMERALS 1 distal direction
2 proximal direction
3 drive mechanism
4 dose setting direction
5 dose dispensing direction
10 drug delivery device 12 cartridge holder
14 cartridge
16 piston
18 barrel
20 needle assembly
24 needle cap
26 protective cap
30 housing
31 threaded support
32 closure
33 recess
34 dose indicating window
35 ledge
36 axial stop
37 feedback element
38 flange portion
39 recess
40 dose setting sleeve
41 protrusion
42 radial stop
43 radial stop
44 threaded portion
45 crown wheel portion
50 drive sleeve
51 gear wheel
52 ratchet member
53 flange portion
54 threaded portion
55 crown wheel portion
56 inner sleeve portion
57 drive sleeve spring element
58 dispensing sleeve spring element
59 flange portion
60 radial stop
61 radial stop
63 protrusion
64 flange portion
65 pin
67 clicking member
68 spring
70 dispensing sleeve
71 proximal face
72 recess
73 extension
75 punched structure
80 receptacle
82 piston rod
84 protrusion
84 thread
86 pressure foot
90 injection button
91 injection spring
92 latch element
93 sidewall
94 ledge
100 dose dial button
102 latch element
104 toothed section
106 inside wall portion
110 dose setting clutch
112 tooth
114 latch element
116 recess
120 toothed ring
122 toothed inner surface
130 dose indicating mechanism
131 branch
132 base
133 branch
134 support section
136 bearing
138 bearing
140 spool
142 spool
144 spool spring
145 gear wheel
146 dose indicating tape
148 number
150 single dose limiting member
152 protrusion
154 stop face
156 clicking member
158 stop face
160 last dose limiting member
162 protrusion
164 stop face
166 stop face
170 spring element

The invention claimed is:

1. A drug delivery device for dispensing a dose of a medicament, the drug delivery device comprising:
an elongate housing;
a cartridge arranged in the housing, the cartridge containing the medicament and comprising a piston to dispense the medicament;
a piston rod configured to be engaged with the piston to displace the piston in a distal direction along a longitudinal axis of the housing;
a drive sleeve extending along the longitudinal axis;
a spring coupled to the drive sleeve such that the drive sleeve is rotatable against a biasing force of the spring during dose setting; and
a dispensing sleeve rotatably engaged with the piston rod and being displaceable along the longitudinal axis relative to the drive sleeve and relative to the housing such that a distal end section of the dispensing sleeve axially abuts the drive sleeve, thereby engaging the dispensing sleeve with the drive sleeve during dose dispensing such that torque on the drive sleeve is transmitted to the dispensing sleeve.

2. The drug delivery device of claim 1, wherein the drive sleeve is displaceable along the longitudinal axis from a dose setting position to a dose dispensing position against a biasing force of a drive sleeve spring element.

3. The drug delivery device of claim 2, wherein the dispensing sleeve is displaceable along the longitudinal axis into an intermediate position to axially engage with the drive sleeve, the dispensing sleeve being further displaceable into a distal stop position to displace the drive sleeve from the dose setting position to the dose dispensing position.

4. The drug delivery device of claim 2, wherein the drive sleeve is axially displaceable relative to the housing in the distal direction from the dose setting position to the dose dispensing position against the biasing force of the drive sleeve spring element, the drive sleeve spring element being coupled to the housing.

5. The drug delivery device of claim 1, wherein a distal end of the dispensing sleeve is configured to be releasably rotatably locked with a distal end of the drive sleeve when the dispensing sleeve is in an intermediate position between a dose setting position of the dispensing sleeve and a dose dispensing position of the dispensing sleeve.

6. The drug delivery device of claim 1, wherein the dispensing sleeve is axially displaceable relative to the housing and relative to the drive sleeve against a biasing force of a dispensing sleeve spring element positioned between the dispensing sleeve and the drive sleeve.

7. A drive mechanism for dispensing a dose of a medicament from a drug delivery device, the drive mechanism comprising:
   a piston rod configured to engage with a piston of a cartridge to displace the piston in a distal direction along a longitudinal axis of a housing of the drug delivery device,
   a drive sleeve extending along the longitudinal axis and being rotatable against a biasing force of a spring during dose setting; and
   a dispensing sleeve rotatably engaged with the piston rod and being displaceable along the longitudinal axis relative to the drive sleeve and relative to the housing of the drug delivery device such that a distal section of the dispensing sleeve axially abuts the drive sleeve, thereby engaging the dispensing sleeve with the drive sleeve during dose dispensing such that torque on the drive sleeve is transmitted to the dispensing sleeve.

8. The drive mechanism of claim 7, wherein the drive sleeve is displaceable along the longitudinal axis from a dose setting position to a dose dispensing position against a biasing force of a drive sleeve spring element.

9. The drive mechanism of claim 8, wherein the dispensing sleeve is displaceable along the longitudinal axis into an intermediate position to axially engage with the drive sleeve, the dispensing sleeve being further displaceable into a distal stop position to displace the drive sleeve from the dose setting position to the dose dispensing position.

10. The drive mechanism of claim 8, wherein the drive sleeve is axially displaceable relative to the housing of the drug delivery device in the distal direction from the dose setting position into the dose dispensing position against the biasing force of the drive sleeve spring element.

11. The drive mechanism of claim 7, wherein a distal end of the dispensing sleeve is configured to be releasably rotatably locked with a distal end of the drive sleeve when the dispensing sleeve is in an intermediate position between a dose setting position of the dispensing sleeve and a dose dispensing position of the dispensing sleeve.

12. The drive mechanism of claim 7, wherein the dispensing sleeve is axially displaceable relative to the housing of the drug delivery device and relative to the drive sleeve against a biasing force of a dispensing sleeve spring element.

13. The drive mechanism of claim 7, wherein an inner wall of the dispensing sleeve and a proximal end of the piston rod are engaged by at least one axially and radially extending protrusion engaged with a correspondingly shaped axially and radially extending recess.

14. The drive mechanism of claim 7, wherein the dispensing sleeve is positioned radially between the piston rod and the drive sleeve.

15. The drive mechanism of claim 7, wherein the dispensing sleeve is displaceable in the distal direction from a dose setting position into a dose dispensing position when an injection button located at a proximal end of the housing of the drug delivery device is depressed.

16. The drive mechanism of claim 7, wherein the dispensing sleeve is axially displaceable relative to the housing of the drug delivery device and is permanently rotatably engaged with the piston rod.

17. The drive mechanism of claim 7, wherein:
   a proximal end of the piston rod is rotatably locked with the dispensing sleeve, and
   a distal end of the piston rod comprises an outer thread threadedly engaged with a threaded support of the housing of the drug delivery device.

18. The drive mechanism of claim 7, further comprising a dose dial member rotatably supported at a proximal end of the housing and being selectively rotatably engageable with a dose setting sleeve extending along the longitudinal axis.

19. The drive mechanism of claim 18, wherein a distal end of the dose setting sleeve is configured to be rotatably engaged with the drive sleeve when the drive sleeve is in a dose setting position.

20. A drug delivery device for dispensing a dose of a medicament, the drug delivery device comprising:
   an elongate housing;
   a cartridge being arranged in the housing, the cartridge containing the medicament and comprising a piston to dispense the medicament;
   a piston rod configured to be engaged with the piston to displace the piston in a distal direction along a longitudinal axis of the housing;
   a drive sleeve extending along the longitudinal axis;
   a spring coupled to the drive sleeve such that the drive sleeve is rotatable against a biasing force of the spring during dose setting;
   a dispensing sleeve rotatably engaged with the piston rod; and
   an injection button configured to engage a proximal end portion of the dispensing sleeve to displace the dispensing sleeve along the longitudinal axis relative to the drive sleeve and relative to the housing, thereby engaging the dispensing sleeve with the drive sleeve during dose dispensing such that torque on the drive sleeve is transmitted to the dispensing sleeve.

21. The drug delivery device of claim 20, further comprising:
   a dose dial member axially fixed relative to the housing and rotatably supported at a proximal end of the housing, the dose dial member being rotatable relative to the housing to rotate the drive sleeve against the biasing force of the spring during the dose setting,
   wherein the dose dial member is distinct from the injection button.

22. The drug delivery device of claim 20, further comprising:
   a dose dial member axially fixed relative to the housing and supported at a proximal end of the housing, and
   a dose setting sleeve extending along the longitudinal axis,
   wherein the dose dial member is configured to be coupled to the dose setting sleeve during the dose setting such that the dose setting sleeve rotates when the dose dial member rotates, and
   wherein the dose dial member is configured to be decoupled from the dose setting sleeve during the dose dispensing.

23. The drug delivery device of claim 20, wherein the injection button is configured to displace the drive sleeve along the longitudinal axis from a dose setting position to a dose dispensing position against a biasing force of a drive sleeve spring element.

24. The drug delivery device of claim 20, wherein the injection button is configured to displace the dispensing sleeve from a dose setting position to an intermediate position and from the intermediate position to a dose dispensing position,
   wherein the dispensing sleeve is configured to be disengaged from the drive sleeve when the dispensing sleeve is in the dose setting position, and engaged to the drive sleeve when the dispensing sleeve is in the intermediate position and when the dispensing sleeve is in the dose dispensing position.

25. A drive mechanism for dispensing a dose of a medicament from a drug delivery device, the drive mechanism comprising:

a piston rod configured to engage with a piston of a cartridge to displace the piston in a distal direction along a longitudinal axis of a housing of the drug delivery device;

a drive sleeve extending along the longitudinal axis and being rotatable against a biasing force of a spring during a dose setting;

a dispensing sleeve rotatably engaged with the piston rod; and an injection button configured to engage a proximal end portion of the dispensing sleeve to displace the dispensing sleeve along the longitudinal axis relative to the drive sleeve and relative to the housing of the drug delivery device, thereby engaging the dispensing sleeve with the drive sleeve during dose dispensing such that torque on the drive sleeve is transmitted to the dispensing sleeve.

26. The drug delivery device of claim 25, further comprising:

a dose dial member axially fixed relative to the housing of the drug delivery device and rotatably supported at a proximal end of the housing of the drug delivery device, the dose dial member being rotatable relative to the housing of the drug delivery device to rotate the drive sleeve against the biasing force of the spring during the dose setting, wherein the dose dial member is distinct from the injection button.

27. The drug delivery device of claim 25, further comprising:

a dose dial member configured to be axially fixed relative to the housing of the drug delivery device and configured to be supported at a proximal end of the housing of the drug delivery device, and a dose setting sleeve extending along the longitudinal axis, wherein the dose dial member is configured to be coupled to the dose setting sleeve during the dose setting such that the dose setting sleeve rotates when the dose dial member rotates, and wherein the dose dial member is configured to be decoupled from the dose setting sleeve during the dose dispensing.

28. The drug delivery device of claim 25, wherein the injection button is configured to displace the drive sleeve along the longitudinal axis from a dose setting position to a dose dispensing position against a biasing force of a drive sleeve spring element.

29. The drug delivery device of claim 25, wherein the injection button is configured to displace the dispensing sleeve from a dose setting position to an intermediate position and from the intermediate position to a dose dispensing position, wherein the dispensing sleeve is configured to be disengaged from the drive sleeve when the dispensing sleeve is in the dose setting position, and engaged to the drive sleeve when the dispensing sleeve is in the intermediate position and when the dispensing sleeve is in the dose dispensing position.

* * * * *